United States Patent
Nelson et al.

(10) Patent No.: US 7,432,067 B2
(45) Date of Patent: Oct. 7, 2008

(54) METHODS OF DETECTION OF MATER PROTEIN AUTOANTIBODIES

(75) Inventors: Lawrence M. Nelson, Burke, VA (US); Zhi-Bin Tong, Potomac, MD (US)

(73) Assignee: The United States of America as represented by the Secretary of the Department of Health and Human Services & The National Institutes of Health, Washington, DC (US)

( * ) Notice: Subject to any disclaimer, the term of this patent is extended or adjusted under 35 U.S.C. 154(b) by 0 days.

(21) Appl. No.: 11/586,075

(22) Filed: Oct. 24, 2006

(65) Prior Publication Data

US 2007/0105153 A1  May 10, 2007

Related U.S. Application Data

(62) Division of application No. 10/399,443, filed as application No. PCT/US01/10981 on Apr. 4, 2001, now Pat. No. 7,217,811.

(60) Provisional application No. 60/241,510, filed on Oct. 18, 2000.

(51) Int. Cl.
*G01N 33/53* (2006.01)
(52) U.S. Cl. ............... 435/7.1; 435/7.92; 424/139.1; 424/811; 530/387.9; 530/806; 530/853
(58) Field of Classification Search .............. None
See application file for complete search history.

(56) References Cited

U.S. PATENT DOCUMENTS

| | | | |
|---|---|---|---|
| 5,480,981 | A | 1/1996 | Goodwin et al. |
| 5,637,300 | A | 6/1997 | Dunbar et al. |
| 6,027,727 | A | 2/2000 | Harris et al. |
| 2004/0043452 | A1 | 3/2004 | Ramkumar et al. |

FOREIGN PATENT DOCUMENTS

WO    WO 02/48362 A2    6/2002

OTHER PUBLICATIONS

Hornbeck et al., Current Protocols in Immunology, Enzyme-Linked Immunosorbent Assays (ELISA), 2000, pp. 11.2.1-11.2.22.*
Wolfe, S.L., Molecular and Cellular Biology, 1993, Wadsworth Publishing Company, pp. 790-793.*
Kuby J., Immunology, 1992, W.H. Freeman and Co., p. 125.*
GenBank accession No. AC011470, deposited by DOE Joint Genome Institute and the Stanford Human Genome Center, publically available on Jul. 15, 2000.*
Bouniol et al., "Endogenous transcription occurs at the 1-cell stage in the mouse embryo," *Experimental Cell Research* 218:57-62, 1995.
Chattopadhyay et al., "Antiovarian antibody in premature ovarian failure," *Indian J. Med. Sci.* 53(6):254-258, Jun. 1999 (*Abstract only*).
Damewood et al., "Circulating antiovarian antibodies in premature ovarian failure," *Obstet. Gynecol.* 68(6):850-854, Dec. 1986 (*Abstract only*).
Damjanovic, "Experimetal autoimmune oophoritis. II. Both lymphoid cells and antibodies are successful in adoptive transfer," *Autoimmunity* 9(3):217-223, 1991, (*Abstract only*).
De Angelo and Michael, "Cellular events associated with autoimmune oophoritis and ovarian tumorigenesis in neonatally thymectomized mice," *J. Reprod. Immunol.* 12(1):63-78, Sep. 1987 (*Abstract onlu*).
De Angelo and Michael, "The effect of antisera to thymosin alpha 1 on the course of autoimmune ovarian dysgenesis in neonatally thymectomized mice," *J. Reprod. Immunol.* 11(1):41-53, May 1987 (*Abstract only*).
Garza et al., "Mechanism of ovarian autoimmunity: induction of T cell and antibody responses by T cell epitope mimicry and epitope spreading," 37(2):87-101, Feb. 1998 (*Abstract only*).
Govind et al., "Delineation of a conserved B cell epitope on bonnet monkey (Macaca radiate) and human zona pellucida glycoprotein-B by monoclonal antibodies demonstrating inhibition of sperm-egg binding," *Biol. Reprod.* 62(1):67-75, Jan. 2000 (*Abstract only*).
Hoek et al., "Premature ovarian failure and ovarian autoimmunity," *Endocr. Rev.* 18(1):107-134, Feb. 1997 (*Abstract only*).
Kalantaridou and Nelson, "Autoimmune Premature Ovarian Failure: Of Mice and Women," *JAMWA* 53(1):18-20, 1998.
Kalantaridou and Nelson, "Premature ovarian failure is not premature menopause," *Ann. NY Acad. Sci.*900:393-402, 2000 (*Abstract only*).
Kobe and Deisenhofer, "Proteins with leucine-rich repeats," *Curr. Opin. Struct. Biol.* 5:409-416, 1995.
Kosiewicz and Michael, "Neonatal thymectomy affects follicle populations before the onset of autoimmune oophoritis in B6A mice," *J. Repro. Fertil.* 88(2):427-440, Mar. 1990 (*Abstract only*).
Lou et al., "Rapid Induction of Autoantibodies by Endogenous Ovarian Antigens and Activated T Cells," *J. Immun.*, 156:3535-3540, May 1, 1996 (*Abstract only*).
Luborsky et al., "Ovarian antibodies, FSH and inhibin B: independent markers associated with unexplained infertility," *Human Reprod.* 15(5):1046-1051, 2000.
Melner and Feltus, "Editorial: AutoImmune Premature Ovarian Failure—Endocrine Aspects of a T Cell Disease," *Endocrin .* 140(8):3401-3403, 1999.
Murray et al., "Reproductive and menstrual history of females with fragile X expansions," *Eur. J. Hum. Genet.* 8(4):247-252, Apr. 2000 (*Abstract only*).

(Continued)

*Primary Examiner*—Michael Szperka
(74) *Attorney, Agent, or Firm*—Klarquist Sparkman, LLP

(57) ABSTRACT

Disclosed herein are novel nucleic acid and protein sequences that are essential to fertility. In particular, human Mater cDNA and protein sequences are provided. Functional MATER is required for female fertility; zygotes that arise from Mater null oocytes do not progress beyond the two-cell stage. Methods are described for detecting an autoimmune response to MATER in a subject by detecting autoantibodies that recognize an epitope of a MATER protein. Also provided are methods for diagnosis of infertility or reduced fertility by detecting presence of MATER protein autoantibodies in a subject. The disclosure also describes kits for detecting MATER autoantibodies comprising MATER protein.

5 Claims, 9 Drawing Sheets

OTHER PUBLICATIONS

Rabinowe et al., "Lymphocyte dysfunction in autoimmune oophoritis. Resumption of menses with corticosteroids," *Am. J. Med.* 81(2):347-350, Aug. 1986 (*Abstract only*).

Sakaguchi et al., "Study on cellular events in postthymectomy autoimmune oophoritis in mice. I. Requirement of Lyt-1 effector cells for oocytes damage after adoptive transfer," *J. Exp. Med.* 156(6):1565-1576, Dec. 1, 1982 (*Abstract only*).

Sakaguchi et al., "Study on cellular events in postthymectomy autoimmune oophoritis in mice. II. Requirement of Lyt-1 cells in normal femalemice for the prevention of oophoritis," *J. Exp. Med.* 156(6):1577-1586, Dec. 1, 1982 (*Abstract only*).

Skolnick et al., "From genes to protein structure and function," *Trends in Biotechnology*, 18:34-39, 2000.

Smith et al., "Effector and regulatory cells in autoimmune oophoritis elicited by neonatal thymectomy," *J. Immunol.* 147(9):2928-2933, Nov. 1, 1999 (*Abstract only*).

Taguchi et al., "Autoimmune oophoritis in thymectomized mice: detection of circulating antibodies against oocytes," *Clin. Exp. Immunol.* 40(3):540-553, Jun. 1980 (*Abstract only*).

Taguchi and Nishizuka, "Autoimmune oophoritis in thymectomized mice: T cell requirement in adoptive cell transfer," *Clin. Exp. Immunol.* 42:324-331, 1980.

Tong et al., "A Mouse Gene Encoding an Oocyte Antigen Associated with Autoimmune Premature Ovarian Failure," *Endocrin.* 140(8):3720-3726, 1999.

Tong et al., "*Mater* encodes a maternal protein in mice with a leucine-rich repeat domain homologous to porcine ribonuclease inhibitor," *Mammal. Gen.* 11:281-287, 2000.

Tong et al., "A human homologue of mouse *Mater*, a maternal effect gene essential for early embryonic development," *Human Reproduction*, 17(4):903-911, 2002.

Tung and Teusche, "Mechanisms of autoimmune disease in the testis and ovary," *Hum. Reprod. Update* 1(1):35-50, Jan. 1995 (*Abstract only*).

Tung et al., "Murine autoimmune oophoritis, epididymoorchitis, and gastritis induced by day 3 thymectomy. Autoantibodies," *Am. J. Pathol.* 126(2):303-314, Feb. 1987 (*Abstract only*).

Van Voorhis and Stovall, "Autoantibodies and infertility: a review of the literature," *J. Reprod. Immunol.* 33:239-256, 1997.

Vegetti et al., "Premature ovarian failure," *Mol. Cell Endorinol.* 161(1-2):53-57, Mar. 30, 2000 (*Abstract only*).

Wheatcroft et al., "Detection of antibodies to ovarian antigens in women with premature ovarian failure," *Clin. Exp. Immunol.* 96(1):122-128, Apr. 1994 (*Abstract only*).

Whisstock et al., "Prediction of protein function from protein sequence and structure," *Quarterly reviews of Biophysics*, 36:307-340, 2003.

Xun et al., "Interspecies-specific ovarian autoantigens involved in neonatal thymectomy-induced murine autoimmune oophoritis," *Am. J. Reprod. Immunol.* 29(4):211-218, May 1993 (*Abstract only*).

Yan et al., "Identification of Premature Ovarian Failure Patients with Underlying Autoimmunity," *J. Womens Health Gend. Based Med.* 9(3):275-287, Apr. 2000.

GenBank Accession No. AAF64393, "maternal-antigen-that-embryos-require protein; MATER; ooplasm-specific protein; OPI [*Mus musculus*]." Apr. 19, 2000 (2 pages).

GenBank Accession No. AC011470, "*Homo sapiens* chromosome 19 clone CTC-490M10, complete sequence." Oct. 18, 1999 (40 pages).

GenBank Accession No. AC012107, "*Homo sapiens* clone RP11-45K21, Working Draft Sequence, 25 unordered pieces." Oct. 21, 1999 (45 pages).

GenBank Accession No. AC023887, "*Homo sapiens* chromosome 15 clone RP11-541M19, Working Draft Clone, 9 unordered pieces." Apr. 21, 2000 (48 pages).

GenBank Accession No. AC024580, "*Homo sapiens* chromosome 19 clone CTD-2621I17, Working Draft Sequence, 69 unordered pieces." May 4, 2000 (32 pages).

GenBank Accession No. AF074018_1, "MATER protein [*Mus musculus*]." May 10, 2000 (2 pages).

GenBank Accession No. AF143559, "*Mus musculus* maternal-antigen-that-embryos-require protein (Mater) gene, exon 1," Apr. 19, 2000 (12 pages).

GenBank Accession No. AV367637, "*Mus musculus* 16 days embryo lung cDNA, RIKEN full-length enriched library, clone:8430436F06, 3' end partial sequence." Nov. 5, 1999 (2 pages).

GenBank Accession No. NM_011860, "*Mus musculus* ooplasm (Op1), mRNA." Feb. 28, 2000 (3 pages).

GenBank Accession No. NP_035990, "ooplasm [*Mus musculus*]." Feb. 26, 2000 (2 pages).

GenBank Accession No. Z86039, "B. taurus mRNA for hypothetical protein (oocyte transcript)," Sep. 11, 1997 (1 page).

http://ugsp.info.nih.gov/BioResearch/iastbest.htm, "Two Things Every Little Girl Wants," downloaded Jul. 27, 2000 (2 pages).

http://www.nih.gov/new/NIH-Record/09_24_96/story07.htm, "Hope for Women Facing Infertility Treatment," downloaded Jul. 27, 2000 (1 page).

http://www.nih.gov/news/pr/jan98/nichd-30.htm, Ovarian Disorder Places Women at Risk for Bone Loss, downloaded Jul. 27, 2000 (2 pages).

\* cited by examiner

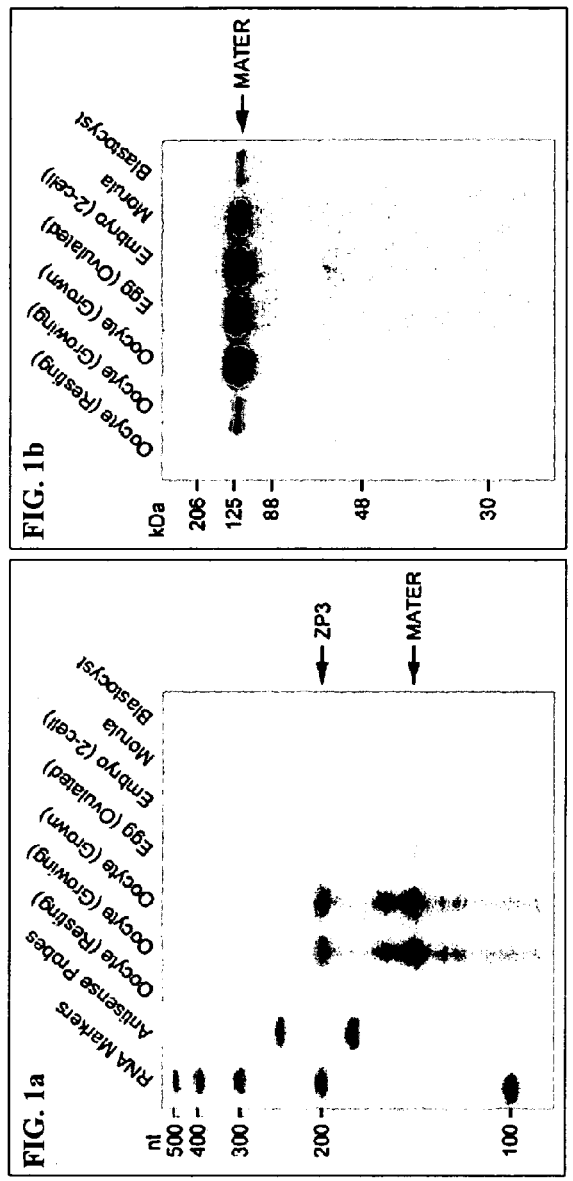
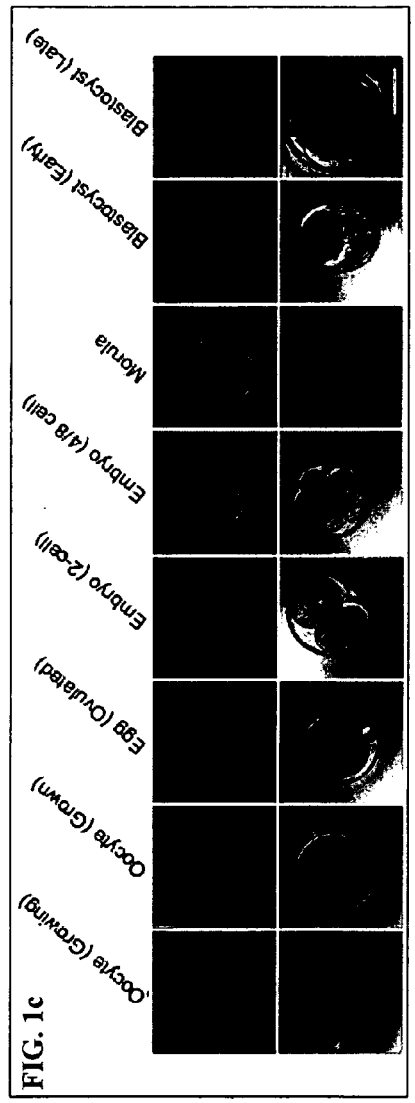

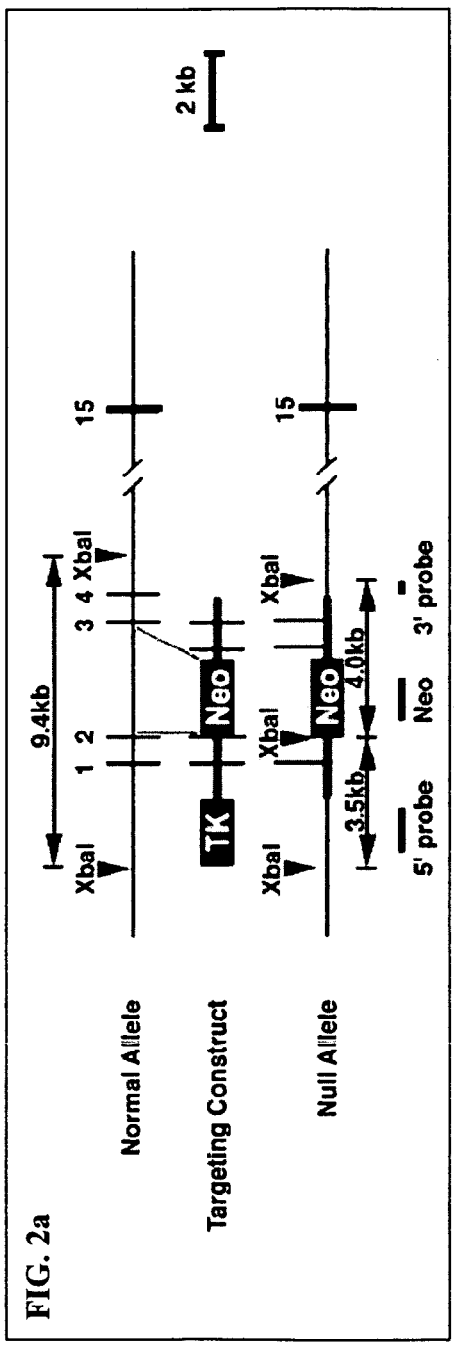
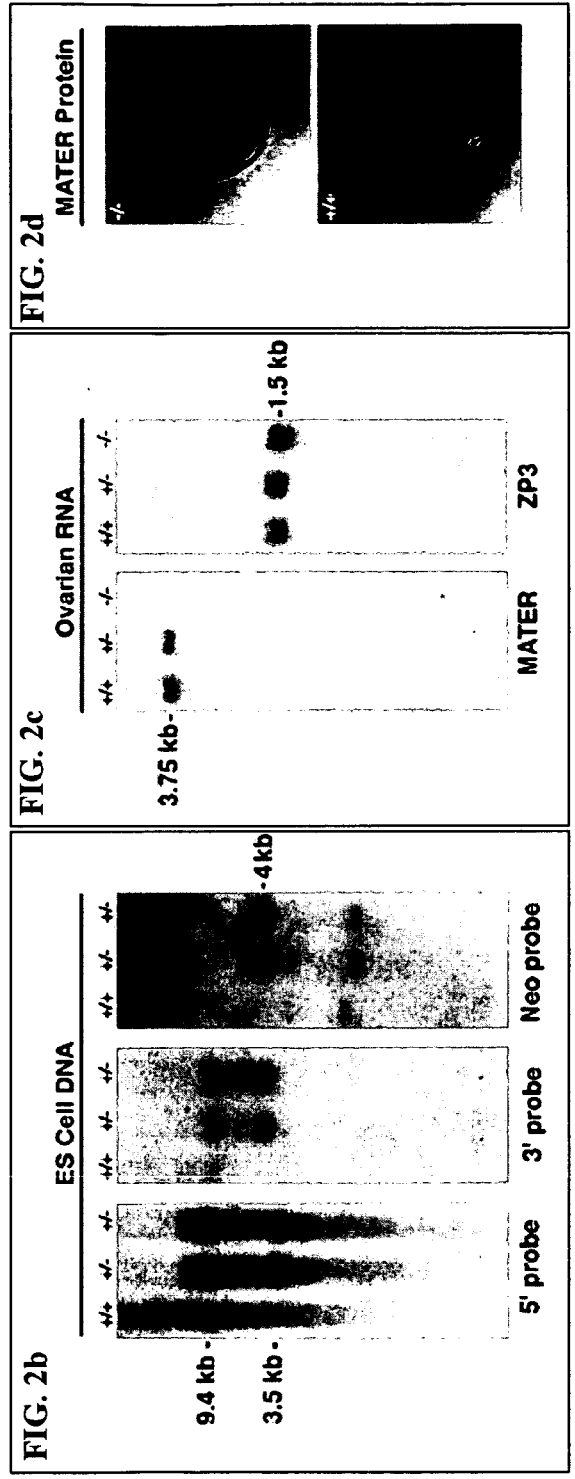
FIG. 2a
FIG. 2b
FIG. 2c
FIG. 2d

FIG. 3a - l
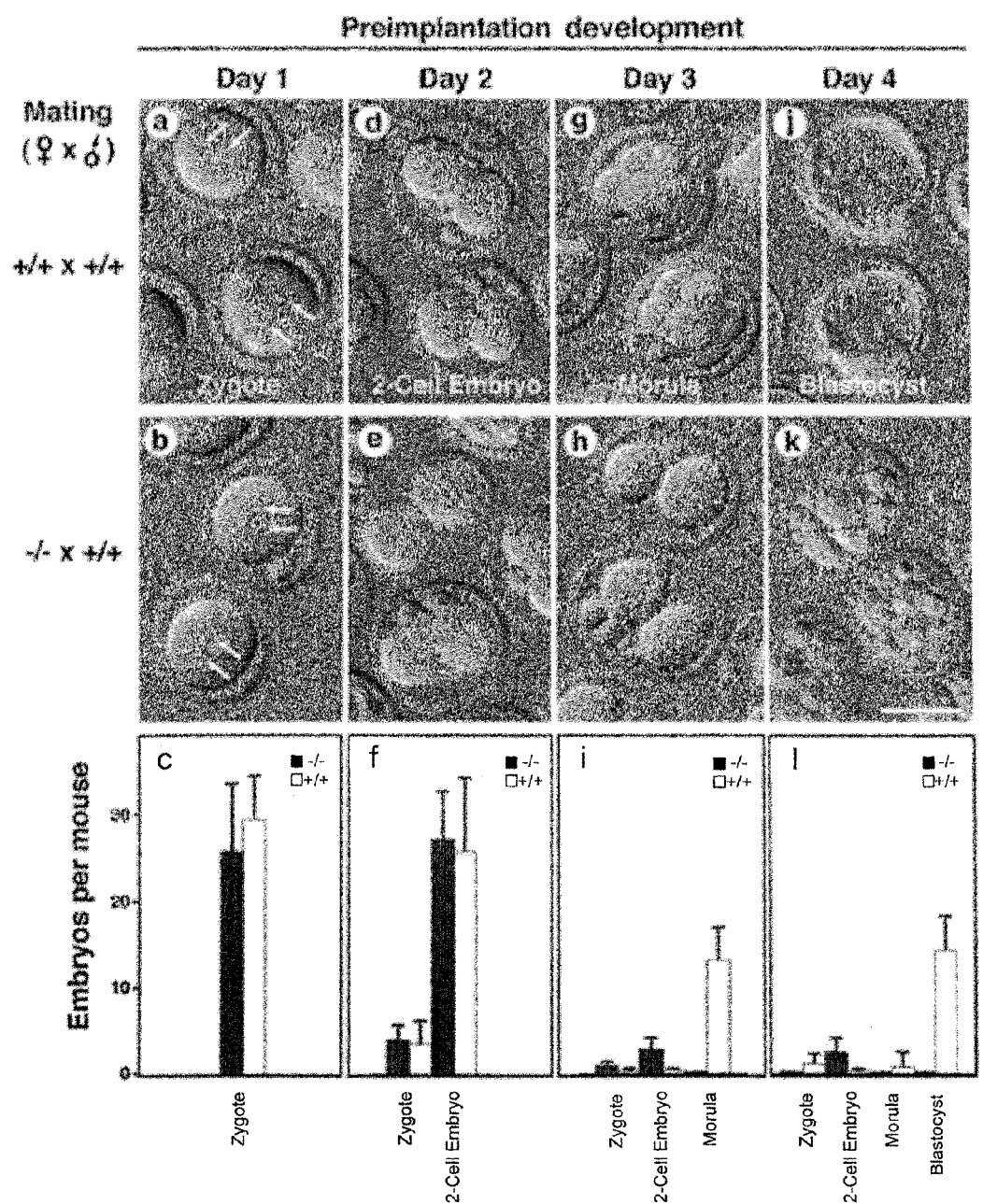

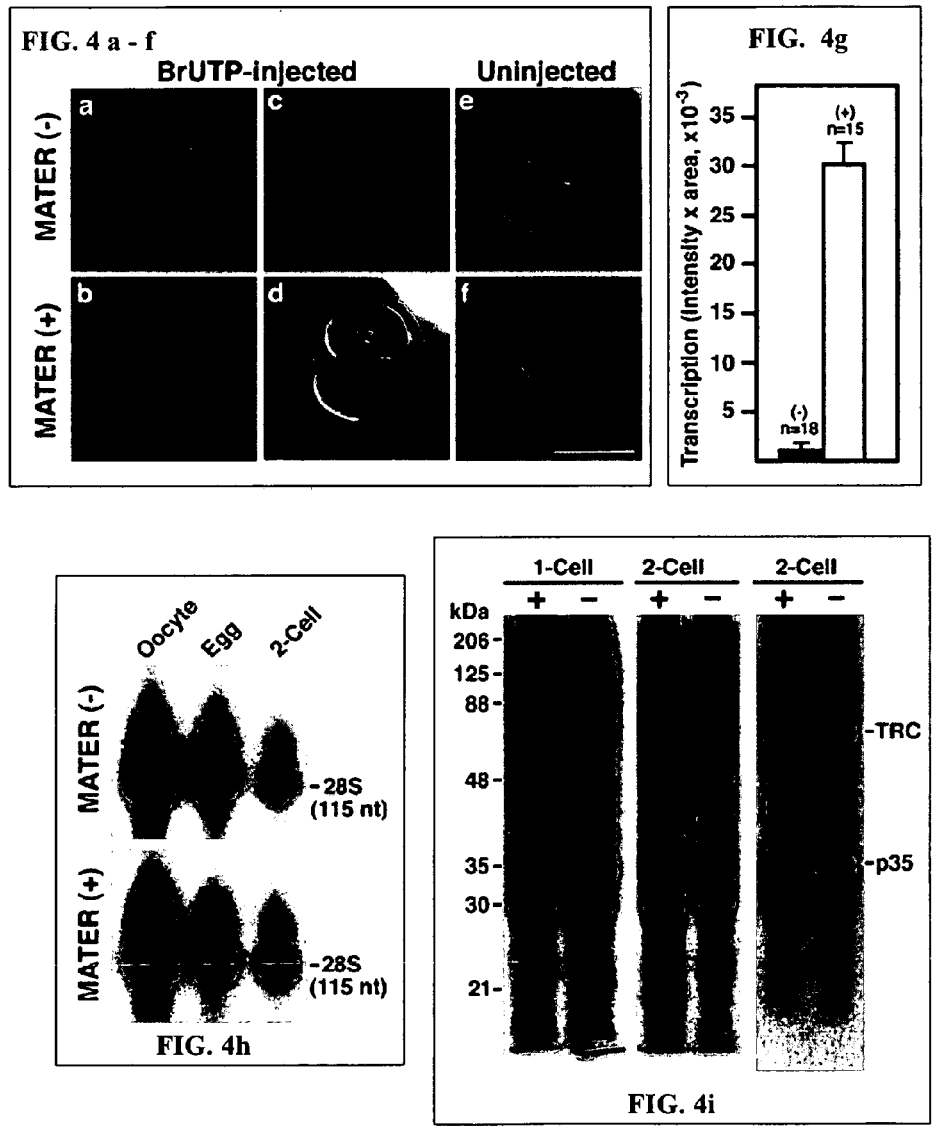

FIG. 9

```
Human:    1                                                                     MKVAGGLELGAA   12
         13  ALLSASPRALVTLSTGPTCSILPKNPLFPQNLSSQPCIKMEGDKSLTFSSYGLQWCLYEL         72
         73  DKEEFQTFKELLKKKSSESTTCSIPQFEIENANVECLALLLHEYYGASLAWATSISIFEN        132

Mouse:    1                                                                     MGPPEKESKAI   11

> # METHODS OF DETECTION OF MATER PROTEIN AUTOANTIBODIES

CROSS-REFERENCE TO RELATED APPLICATIONS

This application is a divisional of Ser. No. 10/399,443, filed Apr. 16, 2003, now U.S. Pat. No. 7,217,811 which is the U.S National Stage of International Application No. PCT/US01/10981, filed Apr. 4, 2001, which claims benefit of U.S. Provisional Application No. 60/241,510, filed Oct. 18, 2000. The disclosures of each of these applications are incorporated herein by reference in its entirety.

FIELD

The present disclosure is generally related to fertility, including the mechanisms controlling it, diseases that arise from defects in such mechanisms, and methods of influencing (either inhibiting or enhancing) fertility.

BACKGROUND

Premature ovarian failure (POF) is a term used to describe certain types of infertility in women. As many as 1% of all women in the United States are thought to be afflicted with POF, which manifests as menopausal-type symptoms, including infertility, in women under the age of 40. Many different diseases and conditions can cause POF, including underlying chromosomal defects (e.g., X-chromosome fragility), chemotherapy, or radiation treatment. Autoimmunity is a well-established mechanism of premature ovarian failure (see Yan et al., *J Womens Health Gend Based Med*. 9:275-87, 2000; and Kalantaridou & Nelson, *J Am Med Womens Assoc*. 53:18-20, 1998). In autoimmune infertility, a woman's ovaries are attacked by cells of her own immune system, leading to a condition known as autoimmune oophoritis (inflammation of the ovary). Autoimmune disease can develop in response to a single inciting antigen and then spread to involve other antigenic molecules of the same organ (Kaufman, *Nature* 366:69-72, 1993). Therefore, identifying the autoantigen target in an organ-specific autoimmune disease is essential to understanding its pathogenesis.

An experimental animal (mouse) model has been used to gain insight into the mechanisms of human autoimmune oophoritis. Removal of the thymus (thymectomy) in neonatal mice (about three days old) induces experimental autoimmune oophoritis in certain strains of mice (Taguchi et al., *Clin Exp Immunol*. 42:324-331, 1980). This experimentally induced condition leads to the production of high levels of anti-ooplasm antibodies and sterility, accompanied by follicular degeneration; the progression of the condition appears to closely parallel human autoimmune oophoritis (Kalantaridou & Nelson, *J Am Med Womens Assoc*. 53:18-20, 1998).

Maternal products control the developmental program until embryonic genome activation takes place. Maternal effect genes that are important in early embryonic development have been well documented in *Drosophila* and *Xenopus* (Morisato & Anderson, *Annu. Rev. Genet*. 29:371-399, 1995; Newport & Kirschner, *Cell* 30:687-696, 1982), but their presence has only been inferred in mammals (Gardner, *Hum. Reprod. Update* 2:1-27, 1999). In mice, embryonic transcription is first detected in the late 1-cell zygote stage and is required for development beyond the 2-cell stage (Schultz, *Bioessays* 15:531-538, 1993; Flach et al., *EMBO J*. 1:681-686, 1982; Latham et al., *Mol. Reprod. Dev*. 35:140-150, 1993). The factors governing this transition from the maternal to the embryonic genome are unknown.

A critical transition in development occurs with the switch from dependence on proteins stored in the egg to those that result from activation of the embryonic genome. This shift which occurs at the two-cell stage in mice is dependent on maternal factors. Gene transcription and protein translation are active during murine oogenesis and RNAs and proteins accumulate within oocytes. However, germ cells become transcriptionally inactive late in oogenesis and much of the maternal RNA is degraded during meiotic maturation and ovulation of the egg into the oviduct. Thus, few maternal gene products persist past the two-cell embryo stage and none have been demonstrated directly to affect early development (Schultz, *Bioessays* 15, 531-538, 1993; Gardner, *Hum. Reprod. Update* 2, 3-27, 1996).

SUMMARY OF THE DISCLOSURE

Described herein is the human MATER protein, an approximately 135 kDa (predicted estimated molecular weight) cytoplasmic protein expressed in mammalian oocytes that is required for female fertility. Zygotes that arise from a MATER null oocyte do not progress beyond the two-cell stage.

Some embodiments are an isolated human MATER protein predicted to have an estimated molecular weight of about 125 kDa to about 135 kDa, in some embodiments more particularly about 134.2 kDa. For instance, this estimated molecular weight may be obtained by SDS-polyacrylamide gel electrophoresis and Western blotting, for instance using an antibody raised against a C-terminal peptide of murine MATER (e.g., residues 1093 to 1111 of SEQ ID NO: 6). MATER proteins include an amino acid sequence as set forth in SEQ ID NOs: 2 or 4 or 24, or a sequence having at least 65% sequence identity with SEQ ID NOs: 2 or 4 or 24. Certain specific examples of such proteins may contain one or more conservative variants within such sequences. The provided human MATER proteins have MATER protein biological activity, for instance in that they can complement a Mater null phenotype.

In certain embodiments, the human MATER protein is an autoantigen associated with autoimmune infertility. The protein may be expressed in oocyte cytoplasm, for instance the oocyte cytoplasm of a mammal such as a human.

One specific embodiment is thus an isolated human MATER protein predicted to have an estimated molecular weight of about 135 kDa, wherein the human MATER protein comprises amino acid sequences as set forth in SEQ ID NO: 2 and/or SEQ ID NO: 4 and/or SEQ ID NO: 24, the protein is an oocyte cytoplasm-specific autoantigen associated with autoimmune infertility, and it can complement a Mater null phenotype by permitting progression of an embryo beyond the two-cell stage.

Further embodiments are isolated nucleic acid molecules that encode such a MATER protein. Examples of such nucleic acid molecules include a sequence as set forth in SEQ ID NOs: 1 or 3 or 23, or a sequence having at least 82% sequence identity with SEQ ID NOs: 1 or 3 or 23. Certain examples of such nucleic acid molecules may contain one or more conservative variants within such sequences. Certain examples hybridize with a nucleic acid probe that includes the sequence shown in SEQ ID NO: 1 or SEQ ID NO: 3 or SEQ ID NO: 23 under wash conditions of 55° C., 0.2×SSC and 0.1% SDS, or under wash conditions of 50° C., 2×SSC, 0.1% SDS.

Also provided are recombinant nucleic acid molecules that include a promoter sequence operably linked to a MATER nucleic acid molecule and cells transformed with such a recombinant nucleic acid molecule.

Methods of detecting a biological condition associated with an abnormal Mater nucleic acid or an abnormal MATER expression or an autoimmune response to MATER in a subject are also provided. Examples of such a biological condition include infertility (such as autoimmune infertility) or reduced fertility, or an increased susceptibility to infertility or reduced fertility. Such methods can involve detecting an abnormal Mater nucleic acid or an abnormal Mater expression or the autoimmune response to MATER in the subject. In specific examples of such methods, the abnormal Mater nucleic acid or abnormal Mater expression includes an alteration in cellular level of Mater nucleic acid or MATER protein, in comparison to a normal level. The abnormal Mater expression may include an increased or decreased expression of Mater in a subject.

Specific provided methods involve determining whether the subject has circulating autoantibodies that recognize an epitope of a MATER protein, wherein presence of such autoantibodies indicates the infertility or reduced fertility of the subject, or an increased susceptibility of the subject to infertility or reduced fertility. Other specific methods involve reacting at least one Mater molecule contained in a clinical sample from the subject with a reagent that includes a Mater specific binding agent (such as an oligonucleotide or a MATER protein specific binding agent (e.g., an antibody or functional fragment thereof)), to form a Mater:agent complex.

Also provided are methods for detecting a predisposition to infertility or reduced fertility or for presymptomatic screening of an individual for infertility or reduced fertility.

Specific methods of detecting a biological condition provided herein involve in vitro amplifying a Mater nucleic acid prior to detecting the abnormal Mater nucleic acid. Amplification can be performed, for instance, using at least one oligonucleotide primer derived from a MATER protein encoding sequence. Examples of such oligonucleotides may include at least 15, for instance at least 20 or at least 23, contiguous nucleotides from SEQ ID NO: 1 or SEQ ID NO: 3 or SEQ ID NO: 23.

Also provided are oligonucleotide primers used in such methods, recombinant DNA vectors that contain such nucleic acid molecules, and recombinant nucleic acid molecules that include a promoter sequence operably linked (in sense or antisense orientation) to such a nucleic acid molecule. Such vectors and recombinant nucleic acid molecules can be transformed into cells or animals (e.g., non-human animals); such transformed cells and animals are also provided.

In certain examples of the provided methods, the Mater molecule is a MATER encoding sequence. In some of such examples, a Mater:agent complex is detected by nucleotide hybridization, for instance where the agent is a labeled nucleotide probe. Such probes may include a sequence as shown in SEQ ID NOs: 1 or 3 or 23, fragments of these sequences (for instance, fragments of 23 or more nucleotides). Other probes may contain a sequence that shares at least 70% sequence identity with a sequence as shown in SEQ ID NOs: 1 or 3 or 23. Such nucleotide probes are also provided.

In other examples of the provided methods, the Mater molecule is a MATER protein, which may contain the sequence of SEQ ID NOs: 2 or 4 or 24, a sequence sharing at least 65% sequence identity with SEQ ID NOs: 2 or 4 or 24, or conservative variants thereof. In some of such examples, Mater:agent complexes are detected by Western blot assay or by ELISA. In certain methods provided, the Mater-specific binding agent is a MATER-specific antibody or a functional fragment thereof, for instance a polyclonal or monoclonal antibody. In specific examples, the antibody recognizes a peptide that includes the sequence of SEQ ID NOs: 2 or 4 or 24, or an antigenic fragment of one of these peptides.

Also provided herein are kits, including kits for detecting an over- or under-abundance of MATER protein or Mater nucleic acid (for instance, in a sample from a subject, such as a mammal), which kits include a MATER protein specific binding agent (such as an antibody or a functional fragment thereof). In certain examples, the agent is capable of specifically binding to an epitope within the amino acid sequence shown in SEQ ID NOs: 2 or 4 or 24, or amino acid sequences that differ from these by one or more conservative amino acid substitutions, or amino acid sequences having at least 65% sequence identity to these sequences, or an antigenic fragment of any of these sequences. Particular examples of such kits further include a means for detecting binding of the MATER protein binding agent to a MATER polypeptide. In certain examples of these kits, the overabundance or underabundance of MATER protein or Mater nucleic acid that is detected results in altered infertility.

Other provided kits are for detecting a genetic mutation (e.g., a mutation in a Mater sequence) in a sample of nucleic acid. Such kits may include an oligonucleotide capable of specifically hybridizing with a Mater nucleic acid (which may be provided in a first container), and a fluorescent labeled nucleic acid probe (for instance, of about 5 to 500 nucleotides) that is fully complementary to the oligonucleotide (which may be provided in a second container).

Specific kit embodiments provided herein are for determining whether or not a subject has a biological condition associated with an abnormal Mater expression by detecting an underabundance of MATER protein in a sample of tissue and/or body fluids from the subject. Such kits include an antibody specific for MATER protein and instructions for using the kit. Such instructions may indicate steps for performing a method to detect the presence of MATER protein in the sample (for instance, using a method described herein); and analyzing data generated by the method, wherein the instructions indicate that underabundance of MATER protein in the sample indicates that the individual has or is predisposed to the biological condition. Specific examples of such kits further include a detectable antibody that binds to the MATER protein specific antibody.

Other specific kit embodiments include a MATER protein specific antibody (which may be provided in a container), a negative control sample which may be provided in a container), instructions for using the kit. Such instructions may indicate steps for performing a test assay to detect a quantity of ATER protein in a test sample of tissue and/or bodily fluid from the subject (such as a test assay provided herein), performing a negative control assay to detect a quantity of MATER protein in the negative control sample; and comparing data generated by the test assay and negative control assay. In specific examples of such kits, the instructions indicate that a quantity of MATER protein in the test sample that is less than the quantity of MATER protein in the negative control sample indicates that the subject has the biological condition. Some of such kits further include a detectable antibody that binds to the antibody specific for MATER protein (which may be provided in a separate container).

Also provided are methods of modifying the level of expression of a MATER protein in a subject, for instance by expressing in the subject a recombinant genetic construct that includes a promoter operably linked (in either sense or antisense orientation) to a nucleic acid molecule that includes at least 23 consecutive nucleotides of SEQ ID NO: 1, SEQ ID NO: 3, SEQ ID NO: 23 or a sequence at least 70% identical to SEQ ID NO: 1, SEQ ID NO: 3, or SEQ ID NO: 23. In particular examples, expression of the nucleic acid molecule changes expression of the MATER protein.

A further embodiment provides methods of screening for a compound useful in influencing MATER-mediated fertility in a mammal. Such methods involve determining if a test compound (for instance, when it is applied to a test cell) binds to or interacts with a MATER protein, such as a human MATER protein, or a variant or fragment thereof, and selecting a compound that so binds. In particular examples of such methods, binding of the compound inhibits a MATER protein biological activity. Also encompassed herein are compounds selected by these methods, for instance such compounds for use as contraceptives or fertility enhancers.

The foregoing and other features and advantages of the invention will become more apparent from the following detailed description of several embodiments, which proceeds with reference to the accompanying figures.

BRIEF DESCRIPTION OF THE FIGURES

FIG. 1 shows two digitized gels, and a series of digitized micrographs, detailing the developmental expression of murine MATER.

FIG. 1A is a digitized image of a Northern blot showing RNase protection of Mater and ZP3 transcripts. RNase protection assays were performed using total RNA from 50 oocytes, eggs or embryos. $^{32}$P-labeled antisense probes and protected fragment lengths for Mater and ZP3 were 180/139 nt and 257/205 nt, respectively.

FIG. 1B is a digitized image of a Western blot, showing MATER protein (approximately 125 kD) amounts in the indicated murine cell types. MATER protein was assayed in 25 oocytes, eggs or embryos by immunoblotting with monospecific antisera to MATER.

FIG. 1C is a series of digitized micrographs, showing the cellular localization of MATER protein. Protein localization was determined using fluorescent labeled antibody, by imaging oocytes, eggs and embryos with laser-scanning confocal microscopy alone (upper images) or after superimposition on a Nomarski image (lower images). Scale bar, 50 µm.

FIG. 2 shows the characterization of targeted Mater locus disruptions.

FIG. 2A is a schematic representation of the normal murine Mater allele (upper), the targeting construct (middle) and the null allele (bottom). The 5' and 3' probes used to assess targeting were outside the region of DNA homology.

FIG. 2B is a series of digitized Northern blots, showing that the Mater null allele was detected in XbaI digested ES cell DNA as a 3.5 kb fragment with the 5' (left) or as a 4.0 kb fragment with the 3' (middle) and neo (right) probes.

FIG. 2C is a pair of digitized Northern blots, showing that Mater transcripts were detected in normal and heterozygous (half the abundance of normal), but not in homozygous null ovaries (left panel). ZP3 transcripts (control) were present in all three genotypes (right panel).

FIG. 2D shows MATER protein expression in wild type and *Mater* null female mice.

FIG. 3 is a series of digitized micrographs and corresponding bar graphs, showing the in vivo development defects of embryos derived from Mater null female mice.

After gonadotrophin induced ovulation, female mice were mated with normal males and oviducts from normal (FIGS. 3A, 3D, 3G, and 3J) or Mater null (FIGS. 3B, 3E, 3H, and 3K) females were flushed one (FIGS. 3A and 3B), two (FIGS. 3D and 3E), three (FIGS. 3G and 3H) and four (FIGS. 3J and 3K) days later. The unfixed embryos were photographed using Nomarski optics. The arrows point to pronuclei in 1-cell zygotes (FIGS. 3A and 3B). Scale bar, 50 µm.

The bar graphs indicate developmental progress of the average number of embryos derived from Mater null (■) and normal (□) females at one (FIG. 3C), two (FIG. 3F), three (FIG. 3I), and four (FIG. 3L) days after mating. Each bar represents the average of 4-5 experiments±s.e.m.

FIG. 4 shows that de novo transcription and translation occurs in murine embryos lacking Mater.

FIG. 4A-4F show digitized micrograph images of murine embryos. Newly synthesized RNA was measured by BrUTP incorporation into the nucleus of one- (FIGS. 4A and 4B) and 2-cell (FIGS. 4C and 4D) embryos derived from Mater null (FIGS. 4A and 4C) and normal (FIGS. 4B and 4D) females using laser-scanning confocal microscopy and a monoclonal antibody to BrUTP.

FIG. 4G is a bar graph, showing the quantity of BrUTP incorporated in 2-cell embryos with (+) and without (−) Mater using arbitrary fluorescence units after subtraction of that obtained with uninjected controls (FIGS. 4E and 4F). Scale bar, 50 µm.

FIG. 4H is a pair of digitized Northern blots, showing RNase protection assays of 28S ribosomal RNA using total RNA from 50 growing oocytes, eggs and 2-cell embryos isolated from females with (+) and without (−) Mater. $^{32}$P-labeled antisense probes and protected fragment lengths for 28S-rRNA were 153 nt and 115 nt, respectively.

FIG. 4I is a series of digitized fluorographs, showing de novo protein synthesis in 1-cell zygotes (left panel) and 2-cell embryos (middle and right panels) that do (+) or do not (−) contain Mater. Each lane contained proteins from 10 embryos that were dissolved in sample buffer directly (left and middle panels) or after partial purification extraction of TRC (65-75 kDa) and p35 (right panels).

FIG. 5 shows ovarian histology, eggs and the number of eggs produced from Mater null females. The number of ovulated eggs and their morphology indicating maturation or degeneration were not remarkably different between normal and Mater null mice.

Figure 5A:
Figure 5B:

FIGS. 5A and 5B are digitized images of ovarian slices from a 4 week old (FIG. 5A) and 8 week old (FIG. 5B) Mater null mouse. The 4 week old Mater null ovarian histology (FIG. 5A) displays different stages of normal ovarian follicles with oogenesis, which are indistinguishable from normal ovarian histology. In the 8 week old sample (FIG. 5B), there are a number of corpora lutea indicating normal spontaneous ovulation, similar to follicular luteinization in the wild-type mouse ovary.

Figure 5C:
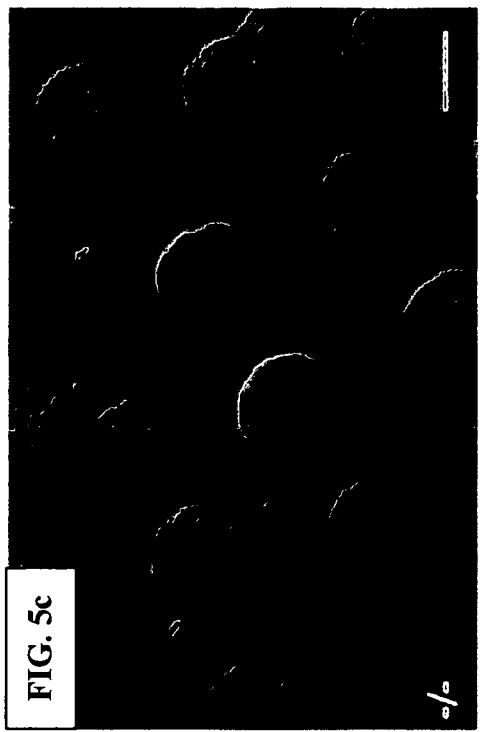

FIG. 5C is a digitized photograph of ovulated eggs from the Mater null mice, produced in response to exogenous PMSG and hCG. Morphology appears similar to that of ovulated eggs from wild-type mice.

Figure 5D:
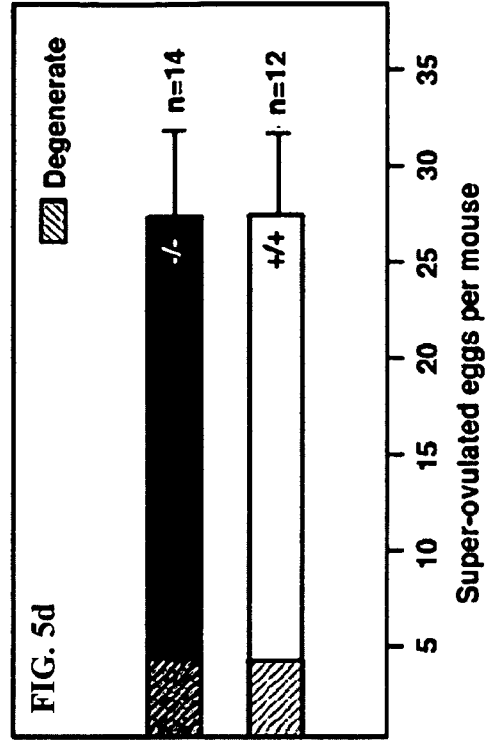

FIG. 5D is a bar graph showing the numbers (mean ±s.e.m.) of the ovulated eggs from the Mater null and wild-type mice.

Figure 6:
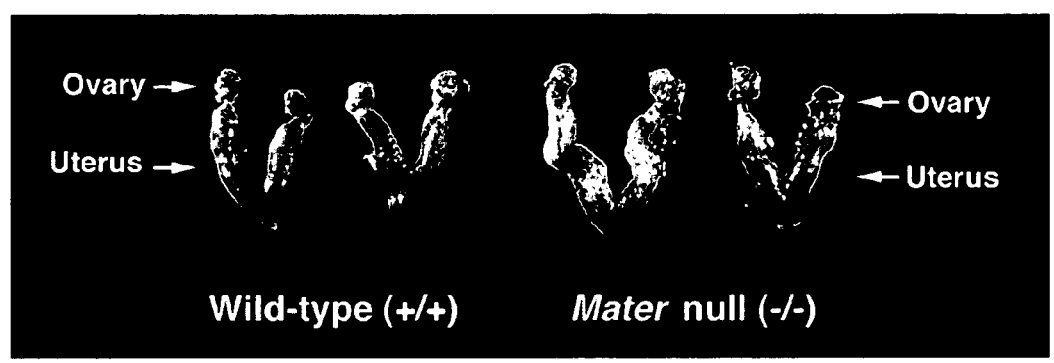

FIG. 6 is a digitized image comparing the gross morphological appearance of the uterus and ovaries of normal and Mater null mice. Ovaries and uteri of Mater null female mice (right) were indistinguishable from the ovaries and uteri from the wild-type female mice (left).

Figure 7:
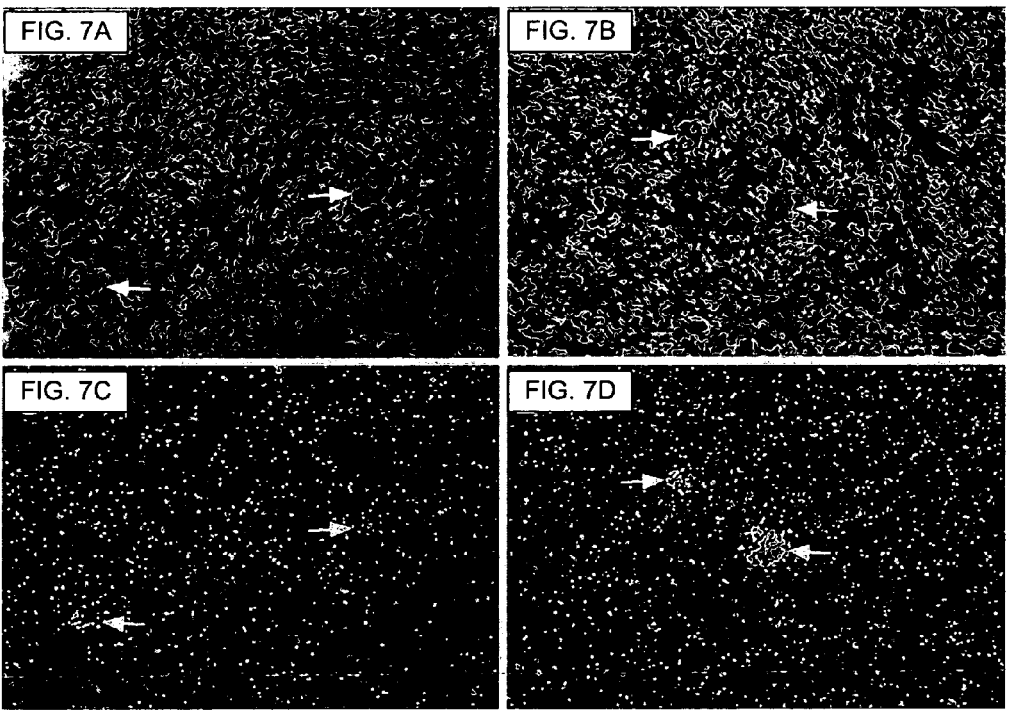

FIG. 7 is a series of digitized micrographs, showing oocyte-specific expression of Mater transcripts in human by in situ hybridization. Both [$^{35}$S]-labeled antisense and sense probes were synthesized by in vitro transcription using the cloned human Mater cDNA as a template. The frozen human ovarian sections were hybridized with the radiolabeled sense (FIGS. 7A and 7C) and antisense (FIGS. 7B and 7D) probes.

The slides were stained with hematoxylin and eosin. For each probe, bright-field (FIGS. 7A and 7B) and dark-field (FIGS. 7C and 7D) images are shown.

Figure 8:
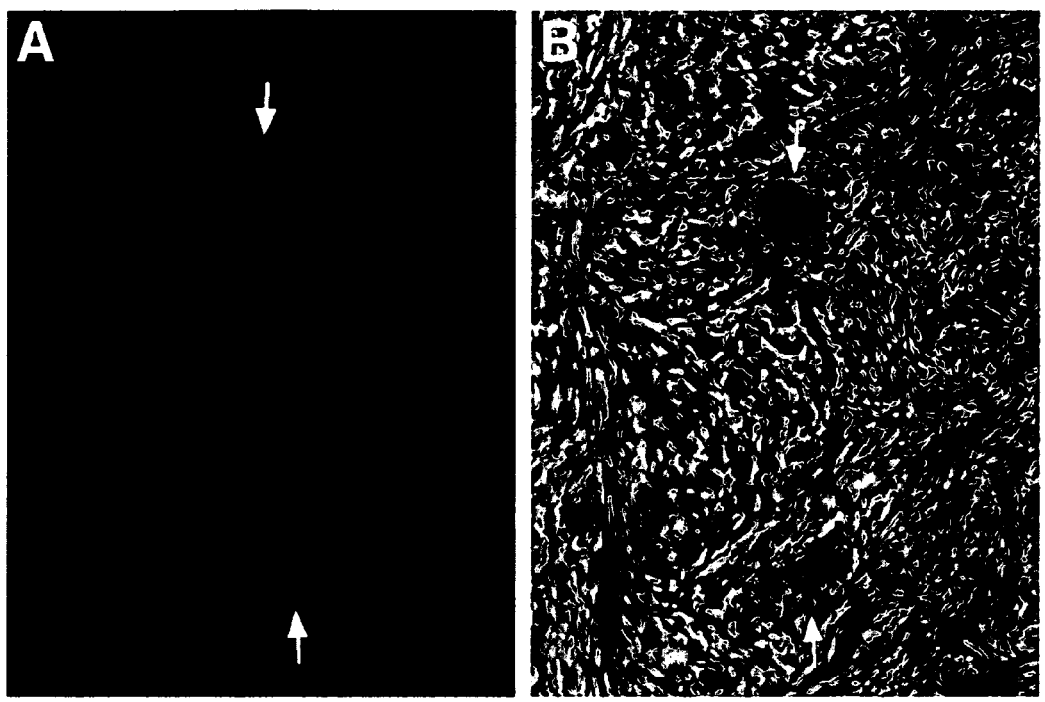

FIG. 8 is a pair of digitized micrographs, showing oocyte-specific expression of human MATER protein. Frozen human ovarian sections were incubated with rabbit antisera (1:200) against a C-terminal peptide of mouse MATER protein, and FITC-conjugated goat anti-rabbit IgG antisera were used as the second antibody to detect human MATER protein in the oocyte (FIG. 8A). The corresponding phase contrast image is shown in FIG. 8B.

FIG. 9 is an alignment of the amino acid sequence of human MATER (SEQ ID NO: 24) and murine MATER (SEQ ID NO: 6) proteins. Identical amino acids are identified; similar amino acids are indicated with a plus (+) symbol.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence of human Mater cDNA fragment 1.

SEQ ID NO: 2 shows the amino acid sequence of the human MATER peptide encoded by fragment 1 (SEQ ID NO: 1).

SEQ ID NO: 3 shows the nucleic acid sequence of human Mater cDNA fragment 2.

SEQ ID NO: 4 shows the amino acid sequence of the human MATER peptide encoded by fragment 2 (SEQ ID No: 3).

SEQ ID NO: 5 shows the nucleic acid sequence of murine Mater cDNA (GenBank Accession number NM_011860.1 and AF074018; individual exons are also listed in AF143559-AF143573).

SEQ ID NO: 6 shows the amino acid sequence of the murine MATER protein (GenBank Accession number NP_035990).

SEQ ID NOs: 7-22 shows several synthetic oligonucleotides useful as probes and/or primers.

SEQ ID NO: 23 shows the nucleic acid sequence of the human Mater cDNA, and the amino acid sequence so encoded.

SEQ ID NO: 24 shows the amino acid sequence of the human MATER protein.

DETAILED DESCRIPTION OF THE DISCLOSURE

I. Abbreviations
ES: embryonic stem
Mater: Maternal Antigen That Embryos Require
OP1: Ooplasm-specific Protein 1
POF: Premature Ovarian Failure
TRC: Transcription Related Complex
ZP3: zona pellucida glycoprotein 3

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Abnormal: Deviation from normal characteristics. Normal characteristics can be found in a control, a standard for a population, etc. For instance, where the abnormal condition is an autoimmune disease condition, such as autoimmune infertility, sources of normal characteristics might include an individual who is not suffering from the autoimmune disorder, a population standard of individuals believed not to be suffering from the disease, etc.

In some examples, abnormal may refer to a condition that is associated with a disease. The term "associated with" includes an increased risk of developing the disease as well as the disease itself. For instance, a certain abnormality (such as an abnormality in a Mater nucleic acid or MATER protein expression) can be described as being associated with the biological conditions of altered (e.g., reduced) fertility and tendency to develop autoimmune infertility.

An abnormal nucleic acid, such as an abnormal Mater nucleic acid, is one that is different in some manner to a normal (wildtype) nucleic acid. Such abnormality includes but is not necessarily limited to: (1) a mutation in the nucleic acid (such as a point mutation (e.g., a single nucleotide polymorphism) or short deletion or duplication of a few to several nucleotides); (2) a mutation in the control sequence(s) associated with that nucleic acid such that replication or expression of the nucleic acid is altered (such as the functional inactivation of a promoter); (3) a decrease in the amount or copy number of the nucleic acid in a cell or other biological sample (such as a deletion of the nucleic acid, either through selective gene loss or by the loss of a larger section of a chromosome or under expression of the mRNA); and (4) an increase in the amount or copy number of the nucleic acid in a cell or sample (such as a genomic amplification of part or all of the nucleic acid or the overexpression of an mRNA), each compared to a control or standard. It will be understood that these types of abnormalities can co-exist in the same nucleic acid or in the same cell or sample; for instance, a genomic-amplified nucleic acid sequence may also contain one or more point mutations. In addition, it is understood that an abnormality in a nucleic acid may be associated with, and in fact may cause, an abnormality in expression of the corresponding protein.

Abnormal protein expression, such as abnormal MATER protein expression, refers to expression of a protein that is in some manner different to expression of the protein in a normal (wildtype) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of a decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8)

alteration of the localized (e.g., organ or tissue specific) expression of the protein (such that the protein is not expressed where it would normally be expressed or is expressed where it normally would not be expressed), each compared to a control or standard.

Controls or standards appropriate for comparison to a sample, for the determination of abnormality, include samples believed to be normal as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Antisense, Sense, and Antigene: Double-stranded DNA (dsDNA) has two strands, a 5'->3' strand, referred to as the plus strand, and a 3'->5' strand (the reverse complement), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding may be detected functionally by determining whether binding has an observable effect upon a biosynthetic process such as expression of a gene, DNA replication, transcription, translation, and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) at which 50% of the target sequence remains hybridized to a perfectly matched probe or complementary strand. A higher ($T_m$) means a stronger or more stable complex relative to a complex with a lower ($T_m$).

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side of the removed sequence being joined together.

Gene amplification or genomic amplification: An increase in the copy number of a gene or a fragment or region of a gene or associated 5' or 3' region, as compared to the copy number in normal tissue. An example of a genomic amplification is an increase in the copy number of an oncogene. A "gene deletion" is a deletion of one or more nucleic acids normally present in a gene sequence and, in extreme examples, can include deletions of entire genes or even portions of chromosomes.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In vitro amplification: Techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Injectable composition: A pharmaceutically acceptable fluid composition including at least one active ingredient. The active ingredient is usually dissolved or suspended in a physiologically acceptable carrier, and the composition can additionally include minor amounts of one or more non-toxic auxiliary substances, such as emulsifying agents, preservatives, and pH buffering agents and the like. Such injectable compositions that are useful for use with the provided nucleotides and proteins are conventional; appropriate formulations are well known in the art.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

MATER protein: A cytosol-localized protein (SEQ ID NO: 24) of approximately 125 to approximately 135 kDa (estimated molecular weight based on gel mobility) that is essential for female fertility. The acronym stands for Maternal Antigen That Embryos Require. Mater is a single-copy gene found on human Chromosome 19. Zygotes that arise from Mater null (Mater$^{-/-}$) oocytes do not progress beyond the two-cell stage. Thus, Mater represents a novel maternal effect gene that is required for embryonic survival and early development in mammals.

Proteins can be identified as MATER proteins by comparing their activity and other physical characteristics to a prototypical MATER protein, such as the human or murine MATER protein. MATER protein biological activity can be described in terms of the ability of a protein to complement (substantially replace the lost function in) a Mater null mutant. The ability of a protein to complement a Mater mutant may be readily determined by introducing the gene encoding the protein into a Mater mutant animal system (such as the Mater null mice described herein) using standard methods. If the encoded protein has MATER protein biological activity, this will be manifested as a proportion of the transgenic progeny animals having a relatively wild-type phenotype for those characteristics linked to the Mater mutant (e.g., infertility of Mater null females due to failure of Mater null oocytes to progress beyond the two-cell stage).

Other MATER protein physical characteristics that can be examined when evaluating a hypothetical MATER protein include the molecular weight of the protein (approximately 125-135 kDa, see Example 1, though this value may vary somewhat from species to species), the subcellular localization of the protein (human MATER is expressed in oocytes (Example 4)), and is predicted to be specifically expressed in the cytoplasm and excluded from the nucleus, as occurs in mice (see Example 1), and the temporal and spatial regulation of the mRNA (Mater transcript is produced in the maturing oocyte, see Examples 1 and 3). Antibodies that recognize one MATER protein (e.g., a murine MATER) may recognize a MATER protein from another species (e.g., human MATER) (see Example 4); thus, hypothetical MATER proteins can be further examined and identified based on recognition by anti-MATER antibodies produced against MATER proteins from other species. The identity of the human MATER protein can therefore be confirmed for instance by immunological identification using an antibody raised against the murine MATER protein, or an epitope of that protein.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, 20, or 23 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with the compositions provided herein are conventional. Martin, *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased gene product. The term polymorphism may be used interchangeably with allele or mutation, unless context clearly dictates otherwise.

Polymorphisms can be referred to, for instance, by the nucleotide position at which the variation exists, by the change in amino acid sequence caused by the nucleotide variation, or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth).

Probes and primers: Nucleic acid probes and primers can be readily prepared based on the nucleic acid molecules provided as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as the Mater sequences described herein, for example, by using computer programs intended for that purpose such as Primer (Version 0.5,© 1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a MATER protein encoding nucleotide will anneal to a target sequence, such as another homolog of the designated MATER protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a MATER protein-encoding nucleotide sequences.

Also provided are isolated nucleic acid molecules that comprise specified lengths of the disclosed Mater nucleotide sequences. Such molecules may comprise at least 10, 15, 20, 23, 25, 30, 35, 40, 45 or 50 or more consecutive nucleotides of these sequences or more, and may be obtained from any region of the disclosed sequences (e.g., a Mater nucleic acid may be apportioned into halves or quarters based on sequence length, and isolated nucleic acid molecules may be derived from the first or second halves of the molecules, or any of the four quarters, etc.). A Mater cDNA or other encoding sequence also can be divided into smaller regions, e.g. about eighths, sixteenths, twentieths, fiftieths and so forth, with similar effect.

Another mode of division is to select the 5' (upstream) and/or 3' (downstream) region associated with a Mater gene.

Nucleic acid molecules may be selected that comprise at least 10, 15, 20, 25, 30, 35, 40, 50 or 100 or more consecutive nucleotides of any of these or other portions of a human Mater nucleic acid molecule, such as those disclosed herein, and associated flanking regions. Thus, representative nucleic acid molecules might comprise at least 10 consecutive nucleotides of the human cDNA fragments shown in SEQ ID NOs: 1 and 2, or the full human MATER cDNA shown in SEQ ID NO: 24.

Protein: A biological molecule expressed by a gene or recombinant or synthetic coding sequence and comprised of amino acids.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of human MATER protein, and the corresponding cDNA or gene sequence, will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and C. elegans sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene*, 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a human MATER protein-encoding sequence will typically hybridize to a probe based on either an entire human MATER protein-encoding sequence or selected portions of the encoding sequence under wash conditions of 2×SSC at 50° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. Thus a protein-specific binding agent binds substantially only the specified protein. By way of example, as used herein, the term "MATER-protein specific binding agent" includes anti-MATER protein antibodies (and functional fragments thereof) and other agents (such as soluble receptors) that bind substantially only to the MATER protein.

Anti-MATER protein antibodies may be produced using standard procedures described in a number of texts, including Harlow and Lane (*Antibodies, A Laboratory Manual*, CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given protein binding agent, such as an anti-MATER protein monoclonal antibody, binds substantially only to the MATER protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Target sequence: "Target sequence" is a portion of ssDNA, dsDNA or RNA that, upon hybridization to a therapeutically effective oligonucleotide or oligonucleotide analog, results in the inhibition of expression. For example, hybridization of therapeutically effectively oligonucleotide to a Mater target sequence results in inhibition of MATER expression. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise defined, all technical and scientific terms used herein have the same meaning as commonly understood by one of ordinary skill in the art to which this invention belongs. The singular terms "a," "an," and "the" include plural referents unless context clearly indicates otherwise. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human MATER Protein and Nucleic Acid Sequences

Embodiments provide MATER proteins and Mater nucleic acid molecules, including cDNA sequences. The prototypical Mater sequences are the murine and human sequences, and the use of these sequences to produce transgenic animals having increased or decreased levels of MATER protein is provided, as are diagnostic methods to detect defects or alterations in Mater expression or MATER protein production.

the full-length cDNA for human Mater(SEQ ID NO:23) is determined to be 3900 base pairs long (which is somewhat longer than the mouse Mater cDNA, GenBank accession# NM_0111860.1, SEQ ID NO:5) and its OFR encodes a protein of 1200 amino acids, having a predicted molecuolar weight of approximately 135.2 kDa and a predicted pI of about 6.08. the human Mater cDNAA comprises the sequences shown in SEQ ID NO:3, which are thought to be aligned approximately with the seventh and eleventh through fifteenth exons of the mouse Mater sequence, respectively. The human Mater mRNA is expressed in oocyres, as shown by in situ hybridization experiments (Example 3).

Human MATER protein (SEQ ID NO: 24) has been specifically localized by immunofluorescence to human oocytes (Example 4). The ATG initiation codon of the Mater cDNA lies within the context of the ANNATG motif associated with vertebrate initiator codon (Kozak, 1991, *J. Biol. Chem.* 266: 19867). The human MATER protein comprises the deduced protein sequences (SEQ ID NOs: 2 and 4) corresponding to the herein described human Mater cDNA sequences (SEQ ID NOs: 1 and 3, respectively). These protein fragments show low but significant sequence homology with the OP1/MATER protein from mouse (GenBank # NP_035990, SEQ ID NO: 6). In particular, SEQ ID NO: 2 is 54% identical to residues 257-638 of murine MATER (SEQ ID NO: 6), while SEQ ID NO: 4 is 64% identical to residues 854-1111 of murine MATER. The overall human MATER protein sequence (SEQ ID NO: 24) shares approximately 50% similarity with the murine MATER protein sequence (SEQ ID NO: 6); the relevant sequence alignment is shown in FIG. 9. The depicted comparison between the human and murine MATER proteins was conducted using the BLAST 2 Sequences Program with parameter conditions of Expect 10 and Filter closed (NIH-NCBI).

Certain regions of the human Mater cDNA have been identified through the sequencing of human HTGSs, though no function or identity had been previously assigned to those sequences. See, for instance, GenBank accession numbers: AC024580 (GI=7705010, published May 4, 2000); AC012107 (GI=6088020, published Oct. 20, 1999, and updated as GI=7329252, published Mar. 28, 2000); and AC023887 (GI=7631054, published Apr. 21, 2000). These fragmentary and overlapping human sequences are up to 207 nucleotides in length and are scattered throughout the murine Mater cDNA sequence. The human ESTs individually share up to 89% identity with the murine Mater cDNA over short, discontinuous regions. Oligonucleotides according to the current disclosure may be chosen to avoid these ESTs. Overall, the first 75 nucleotides of human Mater (1-75) and the corresponding deduced amino acids (1-25) were determined by comparison to published human genomic DNA sequences, while the remainder of the Mater sequence was determined by direct cloning and sequencing of human ovarian cDNAs.

Mater is a single-copy maternal effect gene, the protein product of which is required for early embryonic survival. Although eggs lacking MATER protein can be fertilized, morphologic signs of deterioration are observed as early as the 2-cell stage beyond which the mutant embryos do not progress. The human MATER protein with 1200 amino acids is predicted to have similar molecular domains to those seen in the murine MATER protein (1111 amino acids). As described by Tong et al. (*Mamm. Genome* 11:281-287, 2000), the mouse MATER protein contains a five-fold hydrophilic repeat (26-27 amino acid) near its N-terminus, a short leucine-zipper and a fourteen-fold leucine-rich repeat (28-29 amino acid) near its carboxyl terminus (based on a comparison to the murine MATER protein, as described in Tong et al., *Mamm. Genome* 11, 281-287, 2000). The hydrophilic repeat has low homology with a cytoskeletal protein (neurofilament), raising the possibility that this region mediates interactions that anchor MATER in the cytoplasm. The presence of the leucine-rich domain, as well as a short leucine zipper, both motifs known to mediate protein-protein interactions (Kajava, *J. Mol. Biol.* 277, 519-527, 1998; Buchanan & Gay, *Prog. Biophys. Mol. Biol.* 65, 144, 1996), suggests that MATER may affect embryonic progression through intermediate factor(s), one or more of which binds directly to MATER in the cytoplasm.

Using antisera against a mouse MATER peptide (residues 1093 through 1111 of murine MATER, SEQ ID NO: 6), the inventors have demonstrated that human MATER protein is present in oocytes in human ovary sections (Example 4). Likewise, using mouse-derived nucleotide sense and antisense probes for in situ hybridization experiments, it has been demonstrated that human oocytes express Mater mRNA (Example 3).

The inventors have further characterized murine MATER as to its function in mammalian embryogenesis. This protein is a "maternal" protein, generated in the oocyte prior to fertilization, and therefore encoded for by a maternal gene. MATER is unusual in that it persists (as measured by protein level) into the late blastocyst stage of embryonic development. Functional MATER is required for female fertility; zygotes that arise from Mater null oocytes do not progress beyond the two-cell stage; this is true regardless of what Mater genotype male produced the sperm. The protein is cytoplasmic, with definite exclusion from the nucleus.

The invention is illustrated by the following non-limiting Examples.

EXAMPLE 1

Characterization of the Murine MATER Protein

This example provides several methods for examining MATER proteins and nucleic acids in a mammalian system; the murine system is used.

Methods:

Isolation of oocytes, eggs and embryos. All experiments were conducted in compliance with the guidelines of the Animal Care and Use Committee under an approved animal study protocol. Resting, growing and fully grown oocytes were dissected from 1, 10 and 21 day old (d/o) mouse ovaries, respectively, and eggs were isolated from gonadotrophin stimulated female mice (Tong et al., *J. Biol. Chem.* 270, 849-853, 1995; Rankin et al., *Development* 125, 2415-2424, 1998). Embryos were obtained by mating gonadotrophin stimulated females with males and 1-cell zygotes, 2-cell embryos, morulae and blastocysts were flushed from the oviducts at 1, 2, 3 and 4 days, respectively, counting the morning after hCG administration as day 1. Embryos were either incubated in M16 media (37° C., 5% $CO_2$), fixed in 1% paraformaldehyde for subsequent confocal microscopy, or frozen at −80° C. for RNA and protein analyses. Ovaries were fixed (10% formalin) and embedded in paraffin prior to sectioning and staining with hematoxylin and eosin (American Histolabs, Gaithersburg, Md.).

Detection of transcripts and proteins. Mater, ZP3, β-actin, cyclophilin and 28S-rRNA transcripts were detected by RNase protection assays as previously described (Tong & Nelson, *Endocrinology* 140, 3720-3726, 1999; Tong et al., *J. Biol. Chem.* 270, 849-853, 1995) using an RPA II kit (Ambion, Austin, Tex.).

Rabbits were immunized with a KLH conjugated MATER peptide (amino acids 1093-1111) to obtain a monospecific antisera. After incubating immunoblots with MATER antisera (1:1000, two hours, 20° C.), antibody binding was detected by ECL using a HRP-conjugated goat anti-rabbit antibody (Amersham Pharmacia Biotech, Piscataway, N.J.). Fixed oocytes, eggs or embryos were incubated with MATER antisera (1:8000, 4° C., 16 hours) and imaged by laser-scanning confocal microscopy (LSM 5; Zeiss, Thornwood, N.Y.) using $Cy^5$-conjugated goat anti-rabbit IgG (1:200).

Protein synthesis and immunoblotting. Embryos were incubated in 100 µl of M16 medium containing L-$^{35}$S-methionine (0.5 Ci/ml, Amersham) at 37° C. for 4 hours. At the end of radiolabeling, 1-cell and 2-cell embryos were harvested at 26 hours and 48 hours post-hCG/mating, respectively. After washing with 1% BSA in 10 mM Tris-HCl (pH 7.4), 1 mM EDTA and 140 mM NaCl, ten embryos were dissolved directly in 10 µl of sample buffer (1) directly or (2) after treatment with 2% Triton X-100/0.3 M KCl to extract the TRC and p35 (Conover et al., *Dev. Biol.* 144, 392-404, 1991). After SDS-PAGE and fluorography as previously reported (Tong et al., *J. Biol. Chem.* 270, 849-853, 1995), radioactive incorporation was determined by a phosphoimager and ImageQuant software (Molecular Dynamics, Amersham Pharmacia Biotech, Piscataway, N.J.).

Production of Mater null mice. Constructs used to produce Mater null mice are shown in FIG. 2. To construct a targeting vector in pPNT (Tybulewicz et al., *Cell* 65, 1153-1163, 1991), a 1.5 kbp SacI-EcoRI DNA fragment containing the first two exons of murine Mater (Tong et al., *Mamm. Genome* 11, 281-287, 2000) was inserted between the PGK-Neo and PGK-TK cassettes and a 2 kbp EcoRI-BamHI fragment containing exons 3 and 4 was inserted upstream of the PCK-Neo. After linearization and electroporation into embryonic stem (ES) cells (Redmond et al., *Nat. Genet.* 20, 344-351, 1998), the presence of the mutant allele in chemically selected clones was detected as 3.5 kbp and 4.0 kbp XbaI fragments with 5' and 3' (or Neo) probes, respectively. Both the 5' and 3' probes detected the normal allele as a 9.4 kbp XbaI fragment. C57BL/6 blastocysts were injected with 8-12 ES cells derived from five independently selected clones. Two cell lines that gave rise to coat-color chimeric animals were mated with C57BL/6 females and transmitted the Mater mutation through the germ line. The absence of Mater transcripts in homozygous null females was confirmed by Northern blot analysis as described previously (Tong & Nelson, *Endocrinology* 140, 3720-3726, 1999).

Reproductive performance. Vaginal smears were obtained daily to examine four or more estrus cycles of 6-10 week-old female mice (Rugh, *The Mouse: Its Reproduction and Development* 210 Oxford University Press, Oxford, 1991). Mating behavior was evaluated by the presence of a vaginal plug on the morning after mating with fertile males.

Zygotic gene transcription assays. A 5-10 pl aliquot of 100 mM BrUTP, 140 mM KCl and 2 mM Pipes, pH 7.4 was microinjected into the cytoplasm of embryos isolated 28 hours (1-cell embryos) and 48 hours (2-cell embryos) following hCG and mating, essentially as previously described (Bouniol et al., *Exp. Cell Res.* 218, 57-62, 1995). After incubation in M16 medium in 5% $CO_2$ for one hour at 37° C., injected embryos were fixed in 1% paraformaldehyde.

BrUTP incorporation into RNA was assayed with a mouse anti-BrdU monoclonal antibody (Sigma, 1:1000, 16 hours, 4° C.). After washing in PBS containing 3% BSA, a FITC-conjugated goat anti-mouse IgG antibody was used to image the embryos by confocal microscopy; fluorescence was recorded in arbitrary units. This assay primarily reflects de novo RNA polymerase II activity, because poor penetration of the monoclonal antibody into nucleoli prevents measurement of BrUTP incorporation into ribosomal RNA (Wansink, et al., *J. Cell Biol.* 122, 283-293, 1993).

Results

Mater Transcript and Protein Expression

Mater mRNA was first detected as oocytes entered into their growth phase (30-50 μm) (FIG. 1A). Mater transcripts were most abundant in fully-grown oocytes (75-85 μm) and, like many oocyte transcripts (Bachvarova, in *Developmental Biology: Oogenesis* 1, 453-524, Plenum Press, New York, 1985; Epifano et al., *Development* 121, 1947-1956, 1995), were degraded during meiotic maturation and subsequent ovulation. Mater mRNA was not detected in the early embryo (FIG. 1A), although its presence in EST databases derived from early embryos suggest that some transcripts may have escaped destruction.

The initial accumulation of MATER protein during oogenesis was similar to that observed for Mater transcripts (compare FIG. 1A with FIG. 1B). However, unlike the virtual disappearance of the transcripts, the MATER protein persisted during preimplantation development until the late blastocyst stage (FIG. 1B). Using confocal microscopy, MATER protein was located in the cytoplasm of growing oocytes and noticeably excluded from the nucleus. MATER was more concentrated in the cortical region of oocytes and early embryos (one- and two-cell stages), and this peripheral pattern persisted later in preimplantation development with a higher concentration of MATER in the outer trophectodermal cells compared to the inner cell mass of blastocysts (FIG. 1C).

Mater Null Animals

To determine the function of MATER protein, Mater null mouse lines were generated, in which homozygous females did not express either Mater transcripts or protein. Mater null mice were born in the expected Mendelian ratios with equal sex distribution. No phenotypic abnormalities were observed from birth through adulthood.

Ovaries and uteri from Mater null mice appeared morphologically normal (FIG. 6). Mater null ovaries had a normal complement of primordial follicles and all stages of follicular development were normally represented; corpora lutea, indicating past spontaneous ovulation, were also present (FIG. 5).

Ova lacking Mater were fertilized normally in vivo (FIG. 1). The number and morphology of zygotes and 2-cell embryos from the Mater null females were similar to those from normal females (FIG. 5). However, by 3 or 4 days after mating the embryos from Mater null females still remained at the 2-cell stage or had begun to degenerate (compare FIGS. 3D and 3G with 3E and 3H). Thus, fertilization is normal in Mater null females and the resulting zygotes can progress through the first cleavage, but subsequent development is arrested at the 2-cell stage. This indicates that an arrest of early embryogenesis accounts for the infertility in Mater null females.

Two mouse lines with a Mater null mutation (T54 and T85) were generated (FIGS. 2A and 2B) and neither Mater transcript (FIG. 2C) nor protein (FIG. 2D) were detected in homozygous null females.

Reproductive Phenotype of Mater Null Animals

Matings of heterozygous Mater null parents produced average sized litters (8.5±1.9) with normal Mendelian and equal sex distribution of the null allele in progeny. Homozygous null animals appeared normal and males were as fertile as normal littermates. However, homozygous null females produced no litters, even after five months of mating (Table 1) which implicated Mater as a maternal effect gene.

TABLE 1

Fertility and Mendelian allele ratio of mice with Mater mutation

| Mating pairs | | Litter sizes | Mendelian ratios | | |
|---|---|---|---|---|---|
| ♂ × ♀ | n* | mean ± s.e.m. | +/+ | +/− | −/− |
| Mater$^{+/+}$ × Mater$^{+/+}$ | 11 | 7.5 ± 1.8 | 1.00 | 0 | 0 |
| Mater$^{+/+}$ × Mater$^{+/−}$ | 10 | 7.4 ± 1.9 | n.d.† | n.d. | n.d. |
| Mater$^{+/+}$ × Mater$^{−/−}$ | 9 | 0 | n.a.‡ | n.a. | n.a. |
| Mater$^{−/−}$ × Mater$^{+/+}$ | 8 | 7.6 ± 2.4 | 0 | 1.00 | 0 |
| Mater$^{−/−}$ × Mater$^{+/−}$ | 18 | 8.4 ± 1.9 | 0 | 0.47 | 0.53 |
| Mater$^{+/−}$ × Mater$^{+/−}$ | 15 | 8.5 ± 1.9 | 0.21 | 0.57 | 0.22 |

*n, the number of mating pairs,
†n.d., not done,
‡n.a., not applicable.

Sexually mature Mater null females exhibited regular 5.67±0.22 days estrus cycles, similar to those observed in normal females (5.40±0.23 days). Mating occurred normally, as demonstrated by the appearance of vaginal plugs in about 70% of either Mater null or normal females, after exposure to fertile males. The Mater null ovary had a normal complement of primordial follicles, with all stages of follicular development as well as corpora lutea indicating past spontaneous ovulations (FIGS. 5A and 5B). In addition, the Mater null females ovulated normally after stimulation with exogenous gonadotropins. However, homozygous null females produced no litters even after five months of mating with normal males, while the homozygous null males and heterozygous females had normal fertility.

The mean number (±s.e.m.) of ovulated eggs recovered from null (27.6±4.5, n=14) was not statistically different (p>0.05) from that obtained from normal (27.7±4.3, n=12) females (FIG. 5D). Morphologically, the two groups of eggs were indistinguishable from one another (FIG. 5C).

Fertilization and Embryo Development in Mater Null Animals

To evaluate in vivo fertilization and early development, embryos were isolated from normal and Mater null females at 1, 2, 3 and 4 days after mating with normal males. Fertilization occurred in eggs lacking MATER, as demonstrated by the presence of two pronuclei (arrows, FIGS. 3A and 3B). The number and morphology of 1-cell zygotes and 2-cell embryos obtained in vivo from the Mater null females were similar to those observed from normal females, although the 2-cell mutant embryos appeared less healthy, displaying cytoplasmic granulations (FIG. 3A-3F). Embryos obtained from the Mater null female mice 3 or 4 days after mating still remained at the 2-cell stage (or had begun to degenerate), while embryos from normal mice had progressed to the morula or blastocyst stages, respectively.

An equal percentage (~70%) of fertilized 1-cell zygotes derived from Mater null and normal females progressed in vitro to the 2-cell stage. However, after four days in culture, embryos lacking MATER remained arrested at the 2-cell stage (most were degenerating) (FIG. 3K); embryos from the normal females developed to the blastocyst stage in the same time (FIG. 3J). Thus, although fertilization appears normal and zygotes without MATER can progress through the first cleavage, subsequent embryonic development is arrested at the 2-cell stage.

Characterization of Transcription in Mater Null Animals

The early arrest phenotype seen in Mater null mice is reminiscent of the 2-cell block that occurs after exposure of mouse embryos to α-amanitin (Schultz, *Bioessays* 15:531-538, 1993; Flach et al., *EMBO J.* 1, 681-686, 1982), a mushroom toxin that binds to RNA polymerase II and prevents elongation of transcription beyond dinucleotides (Vaisius & Wieland, *Biochemistry* 21, 3097-3101, 1982). Normal embryonic transcription is first detected late in the 1-cell zygote at a level that is ~20% that of the 2-cell embryo (Aoki et al., *Dev. Biol.* 181, 296-307, 1997), but these nascent transcripts are poorly, if at all, translated into protein (Nothias et al., *EMBO J.* 15, 5715-5725, 1996).

To assess de novo RNA polymerase II activity of the early Mater null embryo, bromo-UTP (BrUTP) incorporation was assayed with a monoclonal antibody specific to BrUTP using laser-scanning confocal microscopy, essentially as described previously (Bouniol et al., *Exp. Cell Res.* 218, 57-62, 1995) (FIG. 4A-4G). Morphologically there was a dramatic difference in the amount of BrUTP detected in the nuclei of normal embryos 28 hours (FIG. 4B) and 48 hours (FIG. 4D) after mating compared to those lacking MATER (FIGS. 4A and 4C). BrUTP incorporation in embryos without MATER was marginally greater than that of uninjected controls (FIGS. 4E and 4F) and de novo transcription was less than 5% than observed in normal 2-cell embryos (FIG. 4G).

Characterization of TRC in Mater Null Animals

During meiotic maturation and ovulation, more than 50% of maternal RNA is lost in normal mice (Bachvarova, in *Developmental Biology: Oogenesis* 1, 453-524, Plenum Press, New York, 1985). This degradative process also occurs in females lacking MATER with loss of ribosomal RNA (FIG. 4H) and at least some mRNAs (β-actin, ZP3, cyclophilin, and GAPDH). Normally, the subsequent activation of the embryonic genome at the 2-cell stage is preceded by the transient transcription and translation of a subset of gene products, some of which form the distinctive Transcription Related Complex (TRC) (Bolton et al., *J. Embryol. Exp. Morphol.* 79:139-163, 1984; Nothias et al., *EMBO J.* 15:5715-5725, 1996; Conover et al., *Dev. Biol.* 144:392-404, 1991). This complex, first observed in the early 2-cell embryo, is not formed in the presence of α-amanitin.

To assay for the TRC, 1- and 2-cell embryos derived from Mater null females mated with normal males were incubated with $^{35}$S-methionine. No global differences in the amount of $^{35}$S-methionine incorporation or in protein profiles were noted in comparing normal 1-cell zygotes and those lacking MATER (FIG. 4I, left panel). Although TRC complexes were detected in embryos without MATER at the 2-cell stage (FIG. 4I, middle and right panels), they appeared somewhat less abundant (~60% of normal), which could reflect abnormal protein synthesis in the embryos lacking MATER. This indicates that MATER is not absolutely critical for initiation of all transcription-translation machinery in early embryos.

Although this striking decrease in transcription could reflect generalized morbidity of the embryo, a similar decrease in 1-cell zygotes, which appear quite healthy, as well as absence of an equally dramatic decrease in de novo protein synthesis (FIG. 4I) suggest that the depressed levels of transcription are due either directly, or indirectly to the absence of MATER.

Proposed Function(s) of Mammalian MATER

The homology of the leucine-rich repeat domain of mammalian MATER protein with porcine ribonuclease inhibitor implies that MATER may act as an inhibitor of cytoplasmic RNase. If this is true, RNA in embryos lacking MATER might be subject to extensive degradation, perhaps an accentuation of the normal turnover of RNA that occurs during the maternal-to-zygotic transition in the early embryo. The degradation of RNAs, including those that encode proteins required for transcription, could account for the phenotype observed in Mater null embryos. This seems unlikely; however, because in the absence mutant embryos incorporate $^{35}$S-methionine into proteins and no major difference in protein profiles are observed in comparison with normal embryos. These results indicate that sufficient mRNA, tRNA and ribosomal RNA are present in the mutant embryos to support protein biosynthesis, although it does not preclude the degradation of a targeted subset of RNA required for early embryonic survival.

Transcription-dependent protein synthesis occurs in two phases in the 2-cell embryo, an early minor activation (24 hours after the first mitotic division) that is characterized by appearance of the TRC proteins, and a later major activation that occurs in $G_2$ (8-10 hours after the first mitotic division). The later activation initiates developmental programs required for progression beyond the 2-cell stage (Schultz, *Bioessays* 15, 531-538, 1993). The observed decrease in embryonic transcription in embryos lacking MATER could result from deterioration of transcription machinery, decreased access to genomic DNA or abnormalities in the chromatin template within the nucleus. However, the presence of the TRC proteins in Mater null animals indicates that MATER is not critical for the early phase of transcription-dependent protein synthesis in 2-cell embryos. It further suggests that the transcription machinery, and its ability to access nuclear DNA, is largely intact in Mater null embryos (as it appears to be in Mater null oocytes, which are also transcriptionally active).

The TRC proteins resulting from the early burst of transcription are associated with the nucleus (Schultz, *Bioessays* 15, 531-538, 1993). These proteins could relieve the late transcriptional repression required for progression beyond the 2-cell stage via mechanisms involving MATER. Additionally, it has been reported that mouse oocytes and 1-cell embryos lack coactivator(s) required for enhancer-dependent transcription in 2-cell embryos (Lawinger et al., *J. Biol. Chem.* 274, 8002-8011, 1999). The nature of these coactivators is unknown; they may arise by modification of pre-existing maternal proteins or from early transcription-dependent protein synthesis in the 2-cell embryo. Such process may involve cytoplasmic MATER. Alternatively, MATER might be involved in one or more interactions that are required for cell cycle progression beyond the 2-cell stage. Identification and characterization of proteins that interact with MATER will provide insights into the role of this maternal protein in promoting embryonic survival and early development.

Mater is the first maternal effect gene demonstrated to play a critical role in early mammalian development and the observed sterile phenotype raises the possibility that the absence of a similar molecule could be a cause of human infertility.

EXAMPLE 2

Identification of the Human Mater cDNA

The human Mater cDNA was identified based on its homology to the mouse Mater cDNA sequence by searching the collection of human High Throughput Genomic (HTG) Sequences, maintained by NCBI and the National Library of Medicine. Using the isolated and discontinuous nucleotide fragments identified in this search, the inventors devised oligonucleotide primers pairs (for instance, SEQ ID NOs: 7 and 8, 19 and 20, and 21 and 22) that were used to amplify Mater sequence from purified human ovarian DNA or mRNA/cDNA, and to isolate a partial cDNA clone from a human cDNA library, using standard techniques.

The sequence of two long fragments of the human Mater cDNA is shown in SEQ ID NO: 1 and 3. Together, these two long cDNA fragments constitute 2213 nucleotides of the complete human Mater cDNA.

The deduced human MATER protein portions encoded cDNA fragment 1 (SEQ ID NO: 1) and fragment 2 (SEQ ID NO: 3) are shown in SEQ ID NOs: 2 and 4, respectively.

Using these sequences, the remainder of the human Mater cDNA has been identified; the sequence of the full length cDNA is shown in SEQ ID NO: 23. Overall, the first 75 nucleotides of human Mater (1-75) and the corresponding deduced amino acids (1-25) were determined by comparison to published human genomic DNA sequences, while the remainder of the Mater sequence was determined by direct cloning and sequencing of human ovarian cDNAs. The complete sequence of the human MATER protein is shown in SEQ ID NO: 24.

EXAMPLE 3

Localization of Human Mater Transcript

This example provides one method for detecting expression of the human Mater transcript.

To produce in situ hybridization probes, human genomic DNA was amplified using the following primers:

```
5'-primer:
5'-TTTCACATGAACATCCTTCTCC-3';    (SEQ ID NO: 7)

3'-primer:
5'-AGTGCTGGAGGCAGAAGGAAG-3'.     (SEQ ID NO: 8)
```

The resultant amplified nucleic acid molecule product size was 496 bp, and is predicted to fall within exon 7 of the human Mater gene, based on comparison to the murine Mater exon-intron map. This fragment was subcloned into pBluscript vector as a DNA template. Both $^{35}$S-UTP-labeled sense and antisense sequences were synthesized by in vitro transcription using T3 and T7 RNA polymerases.

In situ hybridization was carried out essentially as described previously (Tong & Nelson, *Endocrinology* 140: 3720-3726, 1999). Briefly, the probes were prepared by alkaline hydrolysis and hybridized with frozen human ovarian sections at 60° C. for 24 hours. After dipping in Kodak NTB-2 emulsion, the slides were exposed to film for 2-3 days and the autoradiographs developed.

The frozen human ovarian sections were hybridized with the radio-labeled sense (FIGS. 7A and 7C) and antisense (B and D) probes. The slides were stained with hematoxylin and eosin. For each probe, bright-field (A and B) and dark-field (C and D) images are displayed. Mater transcript was localized to oocytes.

EXAMPLE 4

Localization of Human MATER Protein

This example provides one method for examining the localization of human MATER protein.

In situ localization was carried out essentially as described for murine samples (see, Tong and Nelson, *Endocrinology* 140:3720-3726, 1999). Briefly, rabbit polyclonal antibody to a murine MATER C-terminal peptide (residues 1093 through 1111 of SEQ ID NO: 6) was prepared as described in Example 9C. Frozen human ovarian sections were incubated with this antiserum (1:200), and FITC-conjugated goat anti-rabbit IgG antiserum was used as the secondary antibody to detect human MATER protein in the oocyte (FIG. 8A). FIG. 8B shows the phase contrast images corresponding to the samples in FIG. 8A.

EXAMPLE 5

Methods of Making Human Mater cDNA

The original means by which the Mater cDNA was identified and obtained is described above. With the provision of the sequence of the large portions of the MATER protein (SEQ ID NOs: 2 and 4) and encoding nucleic acid molecules (SEQ ID NOs: 1 and 3), nucleotide amplification (such as polymerase chain reaction (PCR)) now may be utilized in a simple method for producing the Mater cDNA.

Total RNA is extracted from human cells by any one of a variety of methods well known to those of ordinary skill in the art. Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992) provide descriptions of methods for RNA isolation. Because MATER is expressed in oocytes, human cell lines derived from oocytes or ovaries can be used as a source of such RNA. The extracted RNA is then used as a template for performing reverse transcription-polymerase chain reaction (RT-PCR) amplification of cDNA. Methods and conditions for RT-PCR are described in Kawasaki et al., (In *PCR Protocols, A Guide to Methods and Applications*, Innis et al. (eds.), 21-27, Academic Press, Inc., San Diego, Calif., 1990).

The selection of amplification primers will be made according to the portion(s) of the cDNA that is to be amplified. Primers may be chosen to amplify a segment of a cDNA or the entire cDNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, the majority of the coding portion of the human MATER cDNA molecule (approximately 2.8 kb) may be amplified using the following combination of primers:

```
5'-primer (part of predicted exon 7):
5'-CAGGAATTGGGAAATCGGCTCTCTAG-3';    (SEQ ID NO.: 9)

3'-primer (end of predicted exon 15):
5'-CCAAATGCTTTGTGTTTATTTAATTCC-3'.   (SEQ ID NO.: 10)
```

One of ordinary skill can use the full length human Mater cDNA sequence provided herein (SEQ ID NO: 23) to devise primers that could be used to amplify the entire cDNA using known techniques.

The following set of four primers can be used to amplify ~950 bp at the 5'-end of human Mater cDNA:

The 5'-primers are the universal adapter primers (ADP) for 5'-RACE-PCR as follows (OriGene Technologies, Inc., Rockville, Md.):

```
ADP1:    5'-CGGAATTCGTCACTCAGCG-3'    (SEQ ID NO.: 11)

ADP2:    5'-AGCGCGTGAATCAGATCG-3'     (SEQ ID NO.: 12)
```

The 3'-primers are gene-specific primers (GSP) for human MATER cDNA within exon 7, as follows:

```
GSP1:
5'-ATTCCCTGGTAGAGTCCACCTTGC-3'        (SEQ ID NO.: 13)

GSP2:
5'-ACAGCACGATCCTTCTGGCTAGAG-3'.       (SEQ ID NO.: 14)
```

GSP1 is used as a primer for reverse transcription of human ovarian RNA to synthesize cDNA. The reverse transcribed cDNAs are then adapted at the 5'-end by ADP1 primer, then amplified for the first round of PCR using ADP1 and GSP1 primers. The second round of PCR amplification is followed using PCR products from the first round as template, and ADP2 and GSP2 as primers.

Fragment 1 of the human Mater cDNA (SEQ ID NO: 1) may be amplified using the following combination of primers:

```
5'-primer:
5'-CAAGCTCCGGTGACGGAGATCAT-3';        (SEQ ID NO.: 15)

3'-primer:
5'-AGCTGGAGGCAGAAGGAAGATG-3'.         (SEQ ID NO.: 16)
```

The 3'-terminal region of the human Mater cDNA molecule (also referred to herein as human Mater cDNA fragment 2, SEQ ID NO: 3) may be amplified using the following combination of primers:

```
5'-primer:
5'-TCTGGCCTCAGCCCTCGTCAGCTTGAC-3';    (SEQ ID NO.: 17)

3'-primer:
5'-CCAAATGCTTTGTGTTTATTTAATTCC-3'.    (SEQ ID NO.: 18)
```

These primers are illustrative only; one skilled in the art will appreciate that many different primers may be derived from the provided cDNA sequence in order to amplify the particular indicated regions of Mater cDNA, as well as to complete the sequence of the human Mater cDNA.

Re-sequencing of PCR products obtained by these amplification procedures is recommended; this will facilitate confirmation of the amplified sequence and will also provide information on natural variation on this sequence in different populations or species. Oligonucleotides derived from the provided Mater sequences may be used in such sequencing methods.

Orthologs of human Mater can be cloned in a similar manner, where the starting material consists of cells taken from a non-human species. Orthologs will generally share at least 80% sequence homology with the disclosed human Mater cDNA. Where the non-human species is more closely related to humans, the sequence homology will in general be greater. Closely related orthologous Mater molecules may share at least 82%, at least 85%, at least 90%, at least 91%, at least 93%, at least 95%, or at least 98% sequence homology with the disclosed human sequences.

Oligonucleotides derived from the human Mater cDNA sequence (SEQ ID NO: 23), or fragments thereof (such as SEQ ID NOs: 1 and 3), are encompassed within the scope of the present disclosure. Preferably, such oligonucleotide primers will comprise a sequence of at least 23 consecutive nucleotides of the Mater nucleic acid sequence. To enhance amplification specificity, oligonucleotide primers comprising at least 25, 30, 35, 40, 45 or 50 consecutive nucleotides of these sequences may also be used. These primers for instance may be obtained from any region of the disclosed sequences. By way of example, the human Mater cDNA, ORF and gene sequences may be apportioned into about halves or quarters based on sequence length, and the isolated nucleic acid molecules (e.g., oligonucleotides) may be derived from the first or second halves of the molecules, or any of the four quarters. The murine Mater cDNA, shown in SEQ ID NO: 5, can be used to illustrate this. The human Mater cDNA is 3447 nucleotides in length and so may be hypothetically divided into about halves (nucleotides 1-1723 and 1724-3447) or about quarters (nucleotides 1-862, 863-1723, 1724-2586 and 2587-3447). The human cDNA can be likewise apportioned, or can be described in terms of the fragments presented herein (e.g., fragment 1, corresponding to around about nucleotide 1700 through around about 1950 of murine Mater; and fragment 2 of the human Mater cDNA, corresponding to the 3'-terminal region of murine Mater cDNA, around about nucleotide 2500 through the polyA tail of the murine Mater cDNA).

Nucleic acid molecules may be selected that comprise at least 15, 20, 23, 25, 30, 35, 40, 50 or 100 consecutive nucleotides of any of these or other portions of the human Mater cDNA. Thus, representative nucleic acid molecules might comprise at least 15 consecutive nucleotides of the human Mater cDNA (SEQ ID NO: 23), or fragment 1 or fragment 2 of the disclosed human Mater coding sequence (SEQ ID NOs: 1 and 3, respectively).

EXAMPLE 6

Cloning of the Mater Genomic Sequence (or Gene)

The Mater cDNA sequence and fragments described above does not contain introns, upstream transcriptional promoter or regulatory regions or downstream transcriptional regulatory regions of the Mater gene. It is possible that some mutations in the Mater gene that may lead to defects in embryo development, infertility, or reduced fertility are not included in the cDNA but rather are located in other regions of the Mater gene. Mutations located outside of the open reading frame that encodes the MATER protein are not likely to affect the functional activity of the protein, but rather are likely to result in altered levels of the protein in the cell. For example, mutations in the promoter region of the Mater gene may prevent transcription of the gene and therefore lead to the complete absence of the MATER protein in the cell.

Additionally, mutations within intron sequences in the genomic gene may also prevent expression of the MATER protein. Following transcription of a gene containing introns, the intron sequences are removed from the RNA molecule in a process termed splicing prior to translation of the RNA molecule which results in production of the encoded protein.

When the RNA molecule is spliced to remove the introns, the cellular enzymes that perform the splicing function recognize sequences around the intron/exon border and in this manner recognize the appropriate splice sites. If there is a mutation within the sequence of the intron close to the junction of the intron with an exon, the enzymes may not recognize the junction and may fail to remove the intron. If this occurs, the encoded protein will likely be defective. Thus, mutations inside the intron sequences within the Mater gene (termed "splice site mutations") may also lead to defects in embryo development. However, knowledge of the exon structure and intronic splice site sequences of the Mater gene is required to define the molecular basis of these abnormalities. The provision herein of the Mater cDNA sequence enables the cloning of the entire Mater gene (including the promoter and other regulatory regions and the intron sequences) and the determination of its nucleotide sequence. With this information in hand, diagnosis of a genetic predisposition to fertility defects based on DNA analysis will comprehend all possible mutagenic events at the Mater locus.

The Mater gene may be isolated by one or more routine procedures, including direct sequencing of one or more BAC or PAC clones that contain the Mater sequence.

With the sequences of human Mater cDNA and gene in hand, primers derived from these sequences may be used in diagnostic tests (described below) to determine the presence of mutations in any part of the genomic Mater gene of a patient. Such primers will be oligonucleotides comprising a fragment of sequence from the Mater gene (intron sequence, exon sequence or a sequence spanning an intron-exon boundary) and may include at least 10 consecutive nucleotides of the Mater cDNA or gene. It will be appreciated that greater specificity may be achieved by using primers of greater lengths. Thus, in order to obtain enhanced specificity, the primers used may comprise 15, 17, 20, 23, 25, 30, 40 or even 50 consecutive nucleotides of the Mater cDNA or gene. Furthermore, with the provision of the Mater intron sequence information the analysis of a large and as yet untapped source of patient material for mutations will now be possible using methods such as chemical cleavage of mismatches (Cotton et al., *Proc. Natl. Acad. Sci. USA* 85:4397-4401, 1985; Montandon et al., *Nucleic Acids Res.* 9:3347-3358, 1989) and single-strand conformational polymorphism analysis (Orita et al., *Genomics* 5:874-879, 1989).

Additional experiments may be performed to identify and characterize regulatory elements flanking the Mater gene. These regulatory elements may be characterized by standard techniques including deletion analyses wherein successive nucleotides of a putative regulatory region are removed and the effect of the deletions are studied by either transient or long-term expression analyses experiments. The identification and characterization of regulatory elements flanking the genomic Mater gene may be made by functional experimentation (deletion analyses, etc.) in mammalian cells by either transient or long-term expression analyses.

It will be apparent to one skilled in the art that either the genomic clone or the cDNA or sequences derived from these clones may be utilized in applications, including but not limited to, studies of the expression of the Mater gene, studies of the function of the MATER protein, the generation of antibodies to the MATER protein diagnosis and therapy of MATER deleted or mutated patients to prevent or treat the defects in embryo development. Descriptions of applications describing the use of Mater cDNA, or fragments thereof, are therefore intended to comprehend the use of the genomic Mater gene.

It will also be apparent to one skilled in the art that homologs of this gene may now be cloned from other species, such as the rat or a monkey, by standard cloning methods. Such homologs will be useful in the production of animal models of onset and development of autoimmune infertility, and early embryogenesis. In general, such orthologous Mater molecules will share at least 70% sequence identity with the human Mater nucleic acid disclosed herein; more closely related orthologous sequences will share at least 75%, at least 80%, at least 90%, at least 95%, or at least 98% sequence identity with this sequence.

EXAMPLE 7

Mater Nucleic Acid and Amino Acid Sequence Variants

With the provision of human MATER protein fragments and corresponding nucleic acid sequences herein, the creation of variants of these sequences is now enabled.

Variant MATER proteins include proteins that differ in amino acid sequence from the human MATER sequences disclosed but that share at least 65% amino acid sequence homology with the provided human MATER protein. Other variants will share at least 70%, at least 75%, at least 80%, at least 90%, at least 95%, or at least 98% amino acid sequence homology. Manipulation of the nucleotide sequence of Mater using standard procedures, including for instance site-directed mutagenesis or PCR, can be used to produce such variants. The simplest modifications involve the substitution of one or more amino acids for amino acids having similar biochemical properties. These so-called conservative substitutions are likely to have minimal impact on the activity of the resultant protein. Table 2 shows amino acids that may be substituted for an original amino acid in a protein, and which are regarded as conservative substitutions.

TABLE 2

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in enzymatic function or other protein features may be obtained by selecting amino acid substitutions that are less conservative than those listed in Table 2. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant MATER encoding sequences may be produced by standard DNA mutagenesis techniques, for example, M13 primer mutagenesis. Details of these techniques are provided in Sambrook et al. (In *Molecular Cloning: A Laboratory Manual*, CSHL, New York, 1989), Ch. 15. By the use of such techniques, variants may be created that differ in minor ways from the human MATER sequences disclosed. DNA molecules and nucleotide sequences that are derivatives of those specifically disclosed herein, and which differ from those disclosed by the deletion, addition, or substitution of nucleotides while still encoding a protein that has at least 82% sequence identity with the human MATER encoding sequence disclosed (SEQ ID NOs: 1 and 3), are comprehended by this disclosure. Also comprehended are more closely related nucleic acid molecules that share at least 80%, at least 85%, at least 90%, at least 95%, or at least 98% nucleotide sequence homology with the disclosed Mater sequences. In their most simple form, such variants may differ from the disclosed sequences by alteration of the coding region to fit the codon usage bias of the particular organism into which the molecule is to be introduced. The full length human Mater cDNA (SEQ ID NO: 23) is also encompassed in the disclosure, and as a molecule that comprises both fragment 1 (SEQ ID NO: 1) and fragment 2 (SEQ ID NO: 3), and encoding the human MATER protein with described physical characteristics and biological properties.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed human MATER protein sequences. For example, because of the degeneracy of the genetic code, four nucleotide codon triplets—(GCT, GCG, GCC and GCA)—code for alanine. The coding sequence of any specific alanine residue within the human MATER protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences that encode a MATER protein, but which vary from the disclosed nucleic acid sequences by virtue of the degeneracy of the genetic code.

Variants of the MATER protein may also be defined in terms of their sequence identity with the prototype human MATER protein. As described above, human MATER proteins share at least 65%, at least 70%, at least 75%, at least 80%, at least 90%, at least 95%, or at least 98% amino acid sequence identity with the human MATER protein (SEQ ID NO: 24) or fragments disclosed herein (such as SEQ ID NOs: 2 and 4). Nucleic acid sequences that encode such proteins/fragments readily may be determined simply by applying the genetic code to the amino acid sequence of an MATER protein or fragment, and such nucleic acid molecules may readily be produced by assembling oligonucleotides corresponding to portions of the sequence.

Nucleic acid molecules that are derived from the human Mater cDNA nucleic acid sequences disclosed include molecules that hybridize under stringent conditions to the disclosed prototypical Mater nucleic acid molecules, or fragments thereof. Stringent conditions are hybridization at 65° C. in 6×SSC, 5× Denhardt's solution, 0.5% SDS and 100 µg/ml sheared salmon testes DNA, followed by 15-30 minute sequential washes in 2×SSC, 0.5% SDS, followed by 1×SSC, 0.5% SDS and finally 0.2×SSC, 0.5% SDS, at 65° C.

Low stringency hybridization conditions (to detect less closely related homologs) are performed as described above but at 50° C. (both hybridization and wash conditions); however, depending on the strength of the detected signal, the wash steps may be terminated after the first 2×SSC wash.

Human Mater nucleic acid encoding molecules (including the cDNA shown in SEQ ID NO: 23 and fragments shown in SEQ ID NOs: 1 and 3, and nucleic acids comprising these sequences), and orthologs and homologs of these sequences, may be incorporated into transformation or expression vectors.

EXAMPLE 8

Expression of MATER Protein

With the provision of human Mater cDNA sequence fragments, and methods for determining and cloning the full length human Mater cDNA, the expression and purification of the MATER protein by standard laboratory techniques is now enabled. Purified human MATER protein may be used for functional analyses, antibody production, diagnostics, and patient therapy. Furthermore, the DNA sequence of the Mater cDNA can be manipulated in studies to understand the expression of the gene and the function of its product. Mutant forms of the human MATER may be isolated based upon information contained herein, and may be studied in order to detect alteration in expression patterns in terms of relative quantities, cellular localization, tissue specificity and functional properties of the encoded mutant MATER protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to MATER proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence. Such antibodies may be specific for epitope tags, which can be added to the expression construct for identification and/or purification purposes.

Intact native protein may also be produced in *E. coli* in large amounts for functional studies. Methods and plasmid vectors for producing fusion proteins and intact native proteins in bacteria are described in Sambrook et al. (Sambrook et al., In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). MATER fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants, and animals (Pursel et al., *Science* 244:1281-1288, 1989), which cells or organisms are rendered transgenic by the introduction of the heterologous Mater cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natil. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with nucleic acid amplification.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci. USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Nati. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses, such as papilloma (Sarver et al., *Mol. Cell Biol.* 1:486-496, 1981) or Epstein-Barr (Sugden et al., *Mol. Cell Biol.* 5:410-413, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357-1370, 1978).

The transfer of DNA into eukaryotic, in particular human or other mammalian cells, is now a conventional technique. Recombinant expression vectors can be introduced into the recipient cells as pure DNA (transfection) by, for example, precipitation with calcium phosphate (Graham and vander Eb, *Virology* 52:466, 1973) or strontium phosphate (Brash et al., *Mol. Cell. Biol.* 7:2013, 1987), electroporation (Neumann et al., *EMBO J.* 1:841, 1982), lipofection (Feigner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Techniques of use in packaging long transcripts can be found in Kochanek et al. (*Proc. Natl. Acad. Sci. USA* 93:5731-5739, 1996) Parks et al. (*Proc. Natl. Acad. Sci. USA* 93:13565-13570, 1996) and Parks and Graham (*J. Virol.* 71:3293-3298, 1997). MATER encoding sequences can also be delivered to target cells in vitro via non-infectious systems, for instance liposomes.

These eukaryotic expression systems can be used for studies of MATER encoding nucleic acids and mutant forms of these molecules, the MATER protein and mutant forms of this protein. Such uses include, for example, the identification of regulatory elements located in the 5' region of the Mater gene on genomic clones that can be isolated from human genomic DNA libraries using the information contained herein. The eukaryotic expression systems also may be used to study the function of the normal complete protein, specific portions of the protein, or of naturally occurring or artificially produced mutant proteins.

Using the above techniques, expression vectors containing the Mater gene sequence or cDNA, or fragments or variants or mutants thereof, can be introduced into human cells, mammalian cells from other species or non-mammalian cells, as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts (as described herein) may be used.

Embodiments described herein thus encompass recombinant vectors that comprise all or part of a MATER encoding sequence, such as the Mater gene or cDNA or variants thereof, for expression in a suitable host. The Mater DNA is operatively linked in the vector to an expression control sequence in the recombinant DNA molecule so that the MATER polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with a vector, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant Mater DNA sequences, similar systems are employed to express and produce the mutant product.

EXAMPLE 9

Production of an Antibody to MATER Protein

Monoclonal or polyclonal antibodies may be produced to either the normal MATER protein or mutant forms of this protein. Optimally, antibodies raised against the MATER protein would specifically detect the MATER protein. That is, such antibodies would recognize and bind the MATER protein and would not substantially recognize or bind to other proteins found in human cells. Antibodies to the human MATER protein may recognize MATER from other species, such as murine MATER, and vice versa.

The determination that an antibody specifically detects the MATER protein is made by any one of a number of standard immunoassay methods; for instance, the Western blotting technique (Sambrook et al., In *Molecular Cloning: A Laboratory Manual*, CSHL, New York, 1989). To determine that a given antibody preparation (such as one produced in a mouse) specifically detects the MATER protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose or PVDF) by Western blotting, and the antibody preparation is incubated with the membrane. After washing the membrane to remove non-specifically bound antibodies, the presence of specifically bound antibodies is detected by the use of (by way of example) an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the MATER protein will, by this technique, be shown to bind to the MATER protein band (which will be localized at a given position on the gel determined by its molecular weight, which is approximately 125 kDa based on gel-mobility estimation for murine MATER). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-MATER protein binding.

Substantially pure MATER protein suitable for use as an immunogen is isolated from the transfected or transformed cells as described above. The concentration of protein in the final preparation is adjusted, for example, by concentration on an Amicon (Millipore, Bedford, Mass.) or similar filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the MATER protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused with mouse myeloma cells using polyethylene glycol, and the excess un-fused cells destroyed by growth of the system on selective media comprising aminopterin (HAT media). Successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall (*Enzymol*. 70(A):419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein (Example 8), which optionally can be modified to enhance immunogenicity. Effective polyclonal antibody production is affected by many factors related both to the antigen and the host species. For example, small molecules tend to be less immunogenic than others and may require the use of carriers and adjuvant, examples of which are known. Also, host animals vary in response to site of inoculations and dose, with either inadequate or excessive doses of antigen resulting in low titer antisera. A series of small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof begins to fall, as determined semi-quantitatively (for example, by double immunodiffusion in agar against known concentrations of the antigen). See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the MATER protein is to use synthetic peptides synthesized on a commercially available peptide synthesizer based upon the predicted amino acid sequence of the MATER protein.

By way of example only, mouse MATER C-terminal peptide (residues 1093 through 1111 of SEQ ID NO: 6) was conjugated with KLH to immunize the female rabbits (two) every two-weeks. Starting from the third immunization, a small amount (~3 ml) of blood was collected from the immunized rabbits to examine the titer of the anti-peptide antibodies using the peptide as antigen and ELISA method. Immunizations continued until the antibodies reached maximal titers, which occurred in about ten immunizations, and then the rabbits were sacrificed to bleed in preparation for the sera. The resultant preparation was used both to characterize murine MATER (Example 1) and human MATER (Example 4).

D. Antibodies Raised by Injection of MATER Encoding Sequence

Antibodies may be raised against the MATER protein by subcutaneous injection of a recombinant DNA vector that expresses the MATER protein into laboratory animals, such as mice. Delivery of the recombinant vector into the animals may be achieved using a hand-held form of the Biolistic system (Sanford et al., *Particulate Sci. Technol.* 5:27-37, 1987), as described by Tang et al. (*Nature* 356:152-154, 1992). Expression vectors suitable for this purpose may include those that express the MATER encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

EXAMPLE 10

DNA-Based Diagnosis

The Mater sequence information presented herein can be used in the area of genetic testing for predisposition to reduced fertility or infertility, such as autoimmune infertility, owing to defects in Mater, such as deletion, duplication or mutation. The gene sequence of the Mater gene, including intron-exon boundaries is also useful in such diagnostic methods. Individuals carrying mutations in the Mater gene (or a portion thereof), or having duplications or heterozygous or homozygous deletions of the Mater gene, may be detected at the DNA level with the use of a variety of techniques. For such a diagnostic procedure, a biological sample of the subject, which biological sample contains either DNA or RNA derived from the subject, is assayed for a mutated, duplicated or deleted Mater gene. Suitable biological samples include samples containing genomic DNA or RNA obtained from body cells, such as those present in peripheral blood, urine, saliva, tissue biopsy, surgical specimen, amniocentesis samples and autopsy material. The detection in the biological sample of either a mutant Mater gene, a mutant Mater RNA, or a duplicated or homozygously or heterozygously deleted Mater gene, may be performed by a number of methodologies, examples of which are discussed below.

One embodiment of such detection techniques for the identification of unknown mutations is the amplification (e.g., polymerase chain reaction amplification) of reverse transcribed RNA (RT-PCR) isolated from a subject, followed by direct DNA sequence determination of the products. The presence of one or more nucleotide differences between the obtained sequence and the prototypical Mater cDNA sequence, and especially, differences in the ORF portion of the nucleotide sequence, are taken as indicative of a potential Mater gene mutation.

Alternatively, DNA extracted from a biological sample may be used directly for amplification. Direct amplification from genomic DNA would be appropriate for analysis of the entire Mater gene including regulatory sequences located upstream and downstream from the open reading frame, or intron/exon borders. Reviews of direct DNA diagnosis have been presented by Caskey (*Science* 236:1223-1228, 1989) and by Landegren et al. (*Science* 242:229-237, 1989).

Other mutation scanning techniques appropriate for detecting unknowns within amplicons derived from DNA or cDNA could also be performed. These techniques include direct sequencing (without sequencing), single-strand conformational polymorphism analysis (SSCP) (for instance, see Hongyo et al., *Nucleic Acids Res.* 21:3637-3642, 1993), chemical cleavage (including HOT cleavage) (Bateman et al., *Am. J. Med. Genet.* 45:233-240, 1993; reviewed in Ellis et al., *Hum. Mutat.* 11:345-353, 1998), denaturing gradient gel electrophoresis (DGGE), ligation amplification mismatch protection (LAMP), and enzymatic mutation scanning (Taylor and Deeble, *Genet. Anal.* 14:181-186, 1999), followed by direct sequencing of amplicons with putative sequence variations.

Further studies of Mater genes isolated from female subjects displaying infertility, particularly autoimmune infertility subjects, or their relatives, may reveal particular mutations, genomic amplifications, or deletions, which occur at a high frequency within this population of individuals. In such case, rather than sequencing the entire Mater gene, DNA diagnostic methods can be designed to specifically detect the most common, or most closely disease-linked, MATER defects.

The detection of specific DNA mutations may be achieved by methods such as hybridization using allele specific oligonucleotides (ASOs) (Wallace et al., CSHL Symp. Quant. Biol. 51:257-261, 1986), direct DNA sequencing (Church and Gilbert, *Proc. Natl. Acad. Sci. USA* 81:1991-1995, 1988), the use of restriction enzymes (Flavell et al., *Cell* 15:25-41, 1978; Geever et al., 1981), discrimination on the basis of electrophoretic mobility in gels with denaturing reagent (Myers and Maniatis, Cold Spring Harbor Symp. Quant. Biol. 51:275-284, 1986), RNase protection (Myers et al., *Science* 230:1242-1246, 1985), chemical cleavage (Cotton et al., *Proc. Natl. Acad. Sci. USA* 85:4397-4401, 1985), and the ligase-mediated detection procedure (Landegren et al., *Science* 241:1077-1080, 1988).

Oligonucleotides specific to normal or mutant sequences are chemically synthesized using commercially available machines. These oligonucleotides are then labeled radioactively with isotopes (such as $^{32}P$) or non-radioactively, with tags such as biotin (Ward and Langer, *Proc. Natl. Acad. Sci. USA* 78:6633-6657, 1981), and hybridized to individual DNA samples immobilized on membranes or other solid supports by dot-blot or transfer from gels after electrophoresis. These specific sequences are visualized by methods such as autoradiography or fluorometric (Landegren et al., *Science* 242:

229-237, 1989) or colorimetric reactions (Gebeyehu et al., *Nucleic Acids Res.* 15:4513-4534, 1987). Using an ASO specific for a normal allele, the absence of hybridization would indicate a mutation in the particular region of the gene, or deleted Mater gene. In contrast, if an ASO specific for a mutant allele hybridizes to a clinical sample, this would indicate the presence of a mutation in the region defined by the ASO.

Sequence differences between normal and mutant forms of the Mater gene may also be revealed by the direct DNA sequencing method of Church and Gilbert (*Proc. Natl. Acad. Sci. USA* 81:1991-1995, 1988). Cloned DNA segments may be used as probes to detect specific DNA segments. The sensitivity of this method is greatly enhanced when combined with nucleic acid amplification, e.g., PCR (Wrichnik et al., *Nucleic Acids Res.* 15:529-542, 1987; Wong et al., *Nature* 330:384-386, 1987; Stoflet et al., *Science* 239:491-494, 1988). In this approach, a sequencing primer that lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, *J. Mol. Biol.* 98:503-517, 1975). DNA fragments carrying the restriction site (either normal or mutant) are detected by their reduction in size or increase in corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels, with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (WO 91/10734; Nagamine et al., *Am. J. Hum. Genet.* 45:337-339, 1989). DNA fragments of different sequence compositions may be distinguished on denaturing formamide gradient gels in which the mobilities of different DNA fragments are retarded in the gel at different positions according to their specific "partial-melting" temperatures (Myers et al., *Science* 230:1242-1246, 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., *Proc. Nat. Acad. Sci. USA* 86:6230-6234, 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If multiple mutations are encountered frequently in the Mater gene, a system capable of detecting such multiple mutations likely will be desirable. For example, a nucleic acid amplification reaction with multiple, specific oligonucleotide primers and hybridization probes may be used to identify all possible mutations at the same time (Chamberlain et al., *Nucl. Acids Res.* 16:1141-1155, 1988). The procedure may involve immobilized sequence-specific oligonucleotide probes (Saiki et al., *Proc. Nat. Acad. Sci. USA* 86:6230-6234, 1989).

EXAMPLE 11

Quantitation of MATER Protein

An alternative method of diagnosing Mater gene deletion, amplification, or mutation is to quantitate the level of MATER protein in the cells of a subject. This diagnostic tool would be useful for detecting reduced levels of the MATER protein that result from, for example, mutations in the promoter regions of the Mater gene or mutations within the coding region of the gene that produce truncated, non-functional or unstable polypeptides, as well as from deletions of the entire Mater gene. Alternatively, duplications of the Mater gene may be detected as an increase in the expression level of this protein. The determination of reduced or increased MATER protein levels would be an alternative or supplemental approach to the direct determination of Mater gene deletion, duplication or mutation status by the methods outlined above.

The availability of antibodies specific to the MATER protein will facilitate the quantitation of cellular MATER protein by one of a number of immunoassay methods, which are well known in the art and are presented in Harlow and Lane (*Antibodies, A Laboratory Manual*, CSHL, New York, 1988).

For the purposes of quantitating the MATER protein, a biological sample of the subject, which sample includes cellular proteins, is required. Such a biological sample may be obtained from body cells, such as those present in peripheral blood, urine, saliva, tissue biopsy, amniocentesis samples, surgical specimens and autopsy material. In particular, female reproductive cells (e.g., ova) or embryos are appropriate samples. Quantitation of MATER protein is achieved by immunoassay and compared to levels of the protein found in healthy cells (e.g., cells from a female known not to suffer from decreased fertility). A significant (e.g., 10% or greater, for instance, 20%, 25%, 30%, 50% or more) reduction in the amount of MATER protein in the cells of a subject compared to the amount of MATER protein found in normal human cells would be taken as an indication that the subject may have deletions or mutations in the Mater gene locus, whereas a significant (e.g., 10% or greater, for instance, 20%, 25%, 30%, 50% or more) increase would indicate that a duplication or enhancing mutation had occurred.

EXAMPLE 12

Detection of Serum Antibody Against MATER Protein

The MATER family of proteins was first identified as autoantibodies involved in the pathogenesis of certain cases of autoimmune infertility. With the provision herein of human MATER protein sequences and encoding nucleic acids, methods for the detection and diagnosis of such fertility failure are now enabled.

Autoantibodies that recognize an epitope of the human MATER protein can be detected in samples from a subject, for instance serum or other fluid, using known immunological techniques. The presence of such autoantibodies (e.g., circulating autoantibodies specific for a MATER epitope) indicates that the subject suffers from MATER-mediated infertility or reduced fertility, or has an increased susceptibility to suffer from one of these conditions.

Many techniques are commonly known in the art for the detection and quantification of antigen. Most commonly, the purified antigen will be bound to a substrate, the antibody of the sample will bind via its Fab portion to this antigen, the substrate will then be washed and a second, labeled antibody will then be added which will bind to the Fc portion of the antibody that is the subject of the assay. The second, labeled antibody will be species specific, i.e., if the serum is from a human, the second, labeled antibody will be anti-human-IgG antibody. The specimen will then be washed and the amount of the second, labeled antibody that has been bound will be detected and quantified by standard methods.

Examples of methods for the detection of antibodies in biological samples, including methods employing dip strips or other immobilized assay devices, are disclosed for instance in the following patents: U.S. Pat. No. 5,965,356 (Herpes simplex virus type specific seroassay); U.S. Pat. No. 6,114,179 (Method and test kit for detection of antigens and/or antibodies); U.S. Pat. No. 6,077,681 (Diagnosis of motor neuropathy by detection of antibodies); U.S. Pat. No. 6,057,097 (Marker for pathologies comprising an auto-immune reaction and/or for inflammatory diseases); and U.S. Pat. No. 5,552,285 (Immunoassay methods, compositions and kits for antibodies to oxidized DNA bases).

EXAMPLE 13

Suppression of MATER Expression

A reduction of MATER protein expression in a transgenic cell may be obtained by introducing into cells an antisense construct based on the Mater encoding sequence, including the human Mater cDNA or fragments thereof (for instance, the cDNA fragments shown in SEQ ID NO: 1 and 3) or gene sequence or flanking regions thereof. For antisense suppression, a nucleotide sequence from a MATER encoding sequence, e.g. all or a portion of the Mater cDNA or gene, is arranged in reverse orientation relative to the promoter sequence in the transformation vector. Other aspects of the vector may be chosen as discussed above (Example 8).

The introduced sequence need not be the full length human Mater cDNA (SEQ ID NO: 23) or gene, and need not be exactly homologous to the equivalent sequence found in the cell type to be transformed. Thus, portions or fragments of the murine cDNA (SEQ ID NO: 5) could also be used to knock out expression of the human Mater gene. Generally, however, where the introduced sequence is of shorter length, a higher degree of homology to the native Mater sequence will be needed for effective antisense suppression. The introduced antisense sequence in the vector may be at least 30 nucleotides in length, and improved antisense suppression typically will be observed as the length of the antisense sequence increases. The length of the antisense sequence in the vector advantageously may be greater than 100 nucleotides, and can be up to about the full length of the human Mater cDNA or gene. For suppression of the Mater gene itself, transcription of an antisense construct results in the production of RNA molecules that are the reverse complement of mRNA molecules transcribed from the endogenous Mater gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous MATER expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Finally, dominant negative mutant forms of MATER may be used to block endogenous MATER activity.

EXAMPLE 14

MATER Knockout and Overexpression Transgenic Animals

Mutant organisms that under-express or over-express MATER protein are useful for research. Such mutants allow insight into the physiological and/or pathological role of MATER in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." For example, a non-Mater promoter inserted upstream of a native Mater gene would be non-native. An extra copy of a Mater gene or other encoding sequence on a plasmid, transformed into a cell, would be non-native, whether that extra copy was Mater derived from the same or a different species.

Mutants may be, for example, produced from mammals, such as mice, that either over-express or under-express MATER protein, or that do not express MATER at all. Overexpression mutants are made by increasing the number of MATER-encoding sequences (such as genes) in the organism, or by introducing a MATER-encoding sequence into the organism under the control of a constitutive or inducible or viral promoter such as the mouse mammary tumor virus (MMTV) promoter or the whey acidic protein (WAP) promoter or the metallothionein promoter. Mutants that under-express MATER may be made by using an inducible or repressible promoter, or by deleting the Mater gene, or by destroying or limiting the function of the Mater gene, for instance by disrupting the gene by transposon insertion.

Antisense genes may be engineered into the organism, under a constitutive or inducible promoter, to decrease or prevent MATER expression, as discussed above in Example 13.

A gene is "functionally deleted" when genetic engineering has been used to negate or reduce gene expression to negligible levels. When a mutant is referred to in this application as having the Mater gene altered or functionally deleted, this refers to the Mater gene and to any ortholog of this gene. When a mutant is referred to as having "more than the normal copy number" of a gene, this means that it has more than the usual number of genes found in the wild-type organism, e.g., in the diploid mouse or human.

A mutant mouse over-expressing MATER may be made by constructing a plasmid having the Mater gene driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

A mutant knockout animal (e.g., mouse) from which the Mater gene is deleted or otherwise disabled can be made by removing coding regions of the Mater gene from embryonic stem cells. The methods of creating deletion mutations by using a targeting vector have been described (see, for instance, Thomas and Capecch, *Cell* 51:503-512, 1987). One specific example of the production of a Mater null mouse is described above, in Example 1.

EXAMPLE 15

Gene Therapy

Gene therapy approaches for combating MATER-mediated fertility defects in subjects, or for causing MATER-mediated infertility in subjects, are now made possible.

Retroviruses have been considered the preferred vector for experiments in gene therapy, with a high efficiency of infection and stable integration and expression (Orkin et al., *Prog. Med. Genet.* 7:130-142, 1988). The full-length Mater gene or cDNA can be cloned into a retroviral vector and driven from either its endogenous promoter or, for instance, from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

Recent developments in gene therapy techniques include the use of RNA-DNA hybrid oligonucleotides, as described by Cole-Strauss, et al. (*Science* 273:1386-1389, 1996). This technique may allow for site-specific integration of cloned sequences, thereby permitting accurately targeted gene replacement.

In addition to delivery of Mater to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

EXAMPLE 16

Identification of Therapeutic Compounds

The human MATER molecules disclosed herein can be used to identify (screen for) compounds that are useful in influencing MATER-mediated fertility in a mammal, either by blocking (inhibiting) the activity of MATER (and thereby reducing fertility) or enhancing MATER activity (and thereby increasing fertility).

Such screening methods can include determining if a test compound binds directly to or otherwise interacts with a MATER protein, or a variant or fragment of a MATER protein. Proteins that do bind to such a molecule are select for further characterization.

In specific embodiments, the compound being tested for activity is applied to a cell, for instance a test cell (e.g., a developing oocyte or embryo of a mammal). The activity of the MATER protein in that test cell is then measured, for instance by determining whether the oocyte or embryo progresses beyond the two-cell stage. If application of the test compound alters proportion of embryos that progress beyond two cells, then that compound is selected as a likely candidate for further characterization. In particular examples, a test agent that opposes or inhibits a MATER activity is selected for further study, for example by exposing the agent to a mammalian female reproductive system in vivo, to determine if in vivo fertility is inhibited. Such identified compounds may be useful as contraceptive agents.

Specific examples of compounds likely to be effective at inhibiting MATER activity, and therefore effective as contraceptives, include antibodies specifically directed to epitopes of the MATER protein. The general concept of immunocontraceptives has been described (see, e.g., U.S. Pat. Nos. 5,637, 300 and 6,027,727, describing contraceptive antibodies directed to proteins of the *zona pellucida*, and incorporated herein by reference).

Alternatively, compounds that increase the proportion of embryos that progress beyond two cells (for instance, in an animal system known to be defective for fertility) are selected for further study as possible fertility enhancing agents. Similar screens can be used to identify compounds that mimic the activity of MATER protein, for instance in a Mater null animal.

In addition, it is suggested that MATER protein perform its function within the cytoplasm through interacting with other unknown protein. Physical blockage of such interaction is expected to arrest the MATER function. Candidates for such interactions are being identified based on interactions in a yeast two-hybrid system (Fields and Songs, *Nature* 340:245, 1989). Once molecular domains for the protein interaction are known, molecules can be designed to specifically inhibit or otherwise interfere with MATER protein interactions with these other proteins.

Compounds selected using these methods are comprehended by this disclosure.

EXAMPLE 17

Kits

Kits are provided which contain the necessary reagents for determining Mater gene copy number, such as probes or primers specific for the Mater gene, as well as written instructions. Kits are also provided to determine abnormal expression of Mater mRNA (i.e., containing probes) or MATER protein (i.e., containing a MATER-specific binding agent).

Instructions provided in the diagnostic kits can include calibration curves or charts to compare with the determined (e.g., experimentally measured) values.

A. Kits for Detection of Mater Genomic Sequences

The nucleotide sequences disclosed herein, and fragments thereof, can be supplied in the form of a kit for use in detection of Mater genomic sequences and/or diagnosis of infertility or reduced fertility. In such a kit, an appropriate amount of one or more of the Mater-specific oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in premeasured single use amounts in individual, typically disposable, tubes or equivalent containers. With such an arrangement, the sample to be tested for the presence of Mater genomic amplification can be added to the individual tubes and in vitro amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several in vitro amplification reactions. Those of ordinary skill in the art know the amount of oligonucleotide primer that is appropriate for use in a single amplification reaction. General guidelines may for instance be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, John Wiley & Sons, New York, 1998).

A kit may include more than two primers, in order to facilitate the PCR in vitro amplification of Mater sequences, for instance the Mater gene, specific exon(s) or other portions of the gene, or the 5' or 3' flanking region thereof.

In some embodiments, kits may also include the reagents necessary to carry out PCR in vitro amplification reactions, including, for instance, DNA sample preparation reagents, appropriate buffers (e.g., polymerase buffer), salts (e.g., magnesium chloride), and deoxyribonucleotides (dNTPs). Written instructions may also be included.

Kits may in addition include either labeled or unlabeled oligonucleotide probes for use in detection of the in vitro amplified Mater sequences. The appropriate sequences for such a probe will be any sequence that falls between the annealing sites of the two provided oligonucleotide primers, such that the sequence the probe is complementary to is amplified during the in vitro amplification reaction.

It may also be advantageous to provide in the kit one or more control sequences for use in the amplification reactions. The design of appropriate positive control sequences is well known to one of ordinary skill in the appropriate art.

B. Kits for Detection of Mater mRNA Expression

Kits similar to those disclosed above for the detection of Mater genomic sequences can be used to detect Mater mRNA expression levels. Such kits may include an appropriate amount of one or more of the oligonucleotide primers for use in reverse transcription amplification reactions, similarly to those provided above, with art-obvious modifications for use with RNA.

In some embodiments, kits for detection of Mater mRNA expression levels may also include the reagents necessary to carry out RT-PCR in vitro amplification reactions, including, for instance, RNA sample preparation reagents (including e.g., an RNAse inhibitor), appropriate buffers (e.g., polymerase buffer), salts (e.g., magnesium chloride), and deoxyribonucleotides (dNTPs). Written instructions may also be included.

Kits in addition may include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction.

It also may be advantageous to provide in the kit one or more control sequences for use in the RT-PCR reactions. The design of appropriate positive control sequences is well known to one of ordinary skill in the appropriate art.

Alternatively, kits may be provided with the necessary reagents to carry out quantitative or semi-quantitative Northern analysis of Mater mRNA. Such kits include, for instance, at least one Mater-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme.

C. Kits for Detection of MATER Protein or Peptide Expression

Kits for the detection of MATER protein expression, include for instance, at least one target-protein-specific (e.g., MATER) binding agent (e.g., a polyclonal or monoclonal antibody or antibody fragment) and may include at least one control. The MATER protein specific binding agent and control may be contained in separate containers. The kits may also include means for detecting MATER:agent complexes, for instance the agent may be detectably labeled. If the detectable agent is not labeled, it may be detected by second antibodies or protein A for example which may also be provided in some kits in one or more separate containers. Such techniques are well known.

Additional components in some kits include instructions for carrying out the assay. Instructions will allow the tester to determine whether MATER expression levels are altered, for instance in comparison to a control sample. Reaction vessels and auxiliary reagents such as chromogens, buffers, enzymes, etc. may also be included in the kits.

By way of example only, an effective and convenient immunoassay kit such as an enzyme-linked immunosorbent assay can be constructed to test anti-MATER antibody in human serum, as reported for detection of non-specific anti-ovarian antibodies (Wheatcroft et al, *Clin. Exp. Immunol.* 96:122-128, 1994; Wheatcroft et al, *Hum. Reprod.* 12:2617-2622, 1997). Expression vectors can be constructed using the human MATER cDNA to produce the recombinant human MATER protein in either bacteria or baculovirus (as described in Example 8). By affinity purification, unlimited amounts of pure recombinant MATER protein can be produced.

An assay kit could provide the recombinant protein as an antigen and enzyme-conjugated goat anti-human IgG as a second antibody as well as the enzymatic substrates. Such kits can be used to test if the patient sera contain antibodies against human MATER.

This disclosure provides Mater nucleic acids and proteins, including the human Mater molecules described above. The disclosure further provides methods employing these molecules, including methods to predict and/or diagnose infertility, reduced fertility, or reproductive failure in females, as well as treatments for such infertility and reduced fertility, and contraceptives. It will be apparent that the precise details of the molecules and methods described may be varied or modified without departing from the spirit of the described invention. The inventors claim all such modifications and variations that fall within the scope and spirit of the claims below.

SEQUENCE LISTING

<160> NUMBER OF SEQ ID NOS: 24

<210> SEQ ID NO 1
<211> LENGTH: 1157
<212> TYPE: DNA
<213> ORGANISM: homo sapiens

<400> SEQUENCE: 1

```
caagctccgg tgacggagat catgtcccga ccagaaaggc tgttgttcat cattgacggt      60
ttcgatgacc tgggctctgt cctcaacaat gacacaaagc tctgcaaaga ctgggctgag     120
aagcagcctc cgttcaccct catacgcagt ctgctgagga aggtcctgct ccctgagtcc     180
ttcctgatcg tcaccgtcag agacgtgggc acagagaagc tcaagtcaga ggtcgtgtct     240
ccccgttacc tgttagttag aggaatctcc ggggaacaaa gaatccactt gctccttgag     300
cgcgggattg gtgagcatca gaagacacaa gggttgcgtg cgatcatgaa caaccgtgag     360
ctgctcgacc agtgccaggt gcccgccgtg ggctctctca tctgcgtggc cctgcagctg     420
caggacgtgg tgggggagag cgtcgccccc ttcaaccaaa cgctcacagg cctgcacgcc     480
gcttttgtgt tcatcagct caccctcga ggcgtggtcc ggcgctgtct caatctggag     540
gaaagagttg tcctgaagcg cttctgccgt atggctgtgg agggagtgtg aataggaag     600
tcagtgtttg acggtgacga cctcatggtt caaggactcg gggagtctga gctccgtgct     660
ctgtttcaca tgaacatcct tctcccagac agccactgtg aggagtacta caccttcttc     720
cacctcagtc tccaggactt ctgtgccgcc ttgtactacg tgttagaggg cctggaaatc     780
gagccagctc tctgccctct gtacgttgag aagacaaaga ggtccatgga gcttaaacag     840
gcaggcttcc atatccactc gctttggatg aagcgtttct tgtttggcct cgtgagcgaa     900
gacgtaagga ggccactgga ggtcctgctg ggctgtcccg ttcccctggg ggtgaagcag     960
aagcttctgc actgggtctc tctgttgggt cagcagccta atgccaccac ccaggagac    1020
accctggacg ccttccactg tcttttcgag actcaagaca aagagtttgt tcgcttggca    1080
ttaaacagct tccaagaagt gtggcttccg attaaccaga acctggactt gatagcatct    1140
tccttctgcc tccagct                                                   1157
```

<210> SEQ ID NO 2
<211> LENGTH: 385
<212> TYPE: PRT
<213> ORGANISM: homo sapiens

<400> SEQUENCE: 2

```
Gln Ala Pro Val Thr Glu Ile Met Ser Arg Pro Glu Arg Leu Leu Phe
1               5                   10                  15

Ile Ile Asp Gly Phe Asp Asp Leu Gly Ser Val Leu Asn Asn Asp Thr
            20                  25                  30

Lys Leu Cys Lys Asp Trp Ala Glu Lys Gln Pro Pro Phe Thr Leu Ile
        35                  40                  45

Arg Ser Leu Leu Arg Lys Val Leu Leu Pro Glu Ser Phe Leu Ile Val
    50                  55                  60
```

```
Thr Val Arg Asp Val Gly Thr Glu Lys Leu Lys Ser Glu Val Val Ser
 65                  70                  75                  80

Pro Arg Tyr Leu Leu Val Arg Gly Ile Ser Gly Glu Gln Arg Ile His
                 85                  90                  95

Leu Leu Leu Glu Arg Gly Ile Gly Glu His Gln Lys Thr Gln Gly Leu
            100                 105                 110

Arg Ala Ile Met Asn Asn Arg Glu Leu Leu Asp Gln Cys Gln Val Pro
        115                 120                 125

Ala Val Gly Ser Leu Ile Cys Val Ala Leu Gln Leu Gln Asp Val Val
    130                 135                 140

Gly Glu Ser Val Ala Pro Phe Asn Gln Thr Leu Thr Gly Leu His Ala
145                 150                 155                 160

Ala Phe Val Phe His Gln Leu Thr Pro Arg Gly Val Val Arg Arg Cys
                165                 170                 175

Leu Asn Leu Glu Glu Arg Val Val Leu Lys Arg Phe Cys Arg Met Ala
            180                 185                 190

Val Glu Gly Val Trp Asn Arg Lys Ser Val Phe Asp Gly Asp Asp Leu
        195                 200                 205

Met Val Gln Gly Leu Gly Glu Ser Glu Leu Arg Ala Leu Phe His Met
    210                 215                 220

Asn Ile Leu Leu Pro Asp Ser His Cys Glu Glu Tyr Tyr Thr Phe Phe
225                 230                 235                 240

His Leu Ser Leu Gln Asp Phe Cys Ala Ala Leu Tyr Tyr Val Leu Glu
                245                 250                 255

Gly Leu Glu Ile Glu Pro Ala Leu Cys Pro Leu Tyr Val Glu Lys Thr
            260                 265                 270

Lys Arg Ser Met Glu Leu Lys Gln Ala Gly Phe His Ile His Ser Leu
        275                 280                 285

Trp Met Lys Arg Phe Leu Phe Gly Leu Val Ser Glu Asp Val Arg Arg
    290                 295                 300

Pro Leu Glu Val Leu Leu Gly Cys Pro Val Pro Leu Gly Val Lys Gln
305                 310                 315                 320

Lys Leu Leu His Trp Val Ser Leu Leu Gly Gln Gln Pro Asn Ala Thr
                325                 330                 335

Thr Pro Gly Asp Thr Leu Asp Ala Phe His Cys Leu Phe Glu Thr Gln
            340                 345                 350

Asp Lys Glu Phe Val Arg Leu Ala Leu Asn Ser Phe Gln Glu Val Trp
        355                 360                 365

Leu Pro Ile Asn Gln Asn Leu Asp Leu Ile Ala Ser Ser Phe Cys Leu
    370                 375                 380

Gln
385

<210> SEQ ID NO 3
<211> LENGTH: 1075
<212> TYPE: DNA
<213> ORGANISM: homo sapiens

<400> SEQUENCE: 3
tctggcctca gccctcgtca gcaaccggag cttgacacac ctgtgcctat ccaacaacag      60
cctggggaac gaaggtgtaa atctactgtg tcgatccatg aggcttcccc actgtagtct     120
gcagaggctg atgctgaatc agtgccacct ggacacggct ggctgtggtt ctcttgcact     180
tgcgcttatg ggtaactcat ggctgacgca cctgagcctt agcatgaacc ctgtggaaga     240
```

-continued

```
caatggcgtg aagcttctgt gcgaggtcat gagagaacca tcttgtcatc tccaggacct    300
ggagttggta aaatgtcatc tcaccgccgc gtgctgtgag agtctgtcct gtgtgatctc    360
gaggagcaga cacctgaaga gcctggatct cacggacaat gccctgggtg acggtggggt    420
tgctgcgctg tgcgagggac tgaagcaaaa gaacagtgtt ctgacgagac tcgggttgaa    480
ggcatgtgga ctgacttctg attgctgtga ggcactctcc ttggcccttt cctgcaaccg    540
gcatctgacc agtctaaacc tggtgcagaa taacttcagt cccaaaggaa tgatgaagct    600
gtgttcggcc tttgcctgtc ccacgtctaa cttacagata attgggctgt ggaaatggca    660
gtaccctgtg caaataagga agctgctgga ggaagtgcag ctactcaagc cccgagtcgt    720
aattgacggt agttggcatt cttttgatga agatgaccgg tactggtgga aaaactgaag    780
atacggaaac ctgccccact cacacccatc tgatggagga actttaaacg ctgttttctc    840
agagcaagct atgcacctgg gagttccttc tcaaagatgg agaatgattt ctgattctca    900
caaagccctc aatggtagtg attcttctgt gttcactcta cgttggttac tggatttgaa    960
ggctagagac cttcaagtca taggactcag tatctgtgaa atgtccgtca tatctcagag   1020
catatagagg gaattaaata aacacaaagc atttggaaaa aaaaaaaaaa aaaaa        1075
```

<210> SEQ ID NO 4
<211> LENGTH: 258
<212> TYPE: PRT
<213> ORGANISM: homo sapiens

<400> SEQUENCE: 4

```
Leu Ala Ser Ala Leu Val Ser Asn Arg Ser Leu Thr His Leu Cys Leu
1               5                   10                  15

Ser Asn Asn Ser Leu Gly Asn Glu Gly Val Asn Leu Leu Cys Arg Ser
            20                  25                  30

Met Arg Leu Pro His Cys Ser Leu Gln Arg Leu Met Leu Asn Gln Cys
        35                  40                  45

His Leu Asp Thr Ala Gly Cys Gly Ser Leu Ala Leu Ala Leu Met Gly
    50                  55                  60

Asn Ser Trp Leu Thr His Leu Ser Leu Ser Met Asn Pro Val Glu Asp
65                  70                  75                  80

Asn Gly Val Lys Leu Leu Cys Glu Val Met Arg Glu Pro Ser Cys His
                85                  90                  95

Leu Gln Asp Leu Glu Leu Val Lys Cys His Leu Thr Ala Ala Cys Cys
            100                 105                 110

Glu Ser Leu Ser Cys Val Ile Ser Arg Ser Arg His Leu Lys Ser Leu
        115                 120                 125

Asp Leu Thr Asp Asn Ala Leu Gly Asp Gly Val Ala Ala Leu Cys
    130                 135                 140

Glu Gly Leu Lys Gln Lys Asn Ser Val Leu Thr Arg Leu Gly Leu Lys
145                 150                 155                 160

Ala Cys Gly Leu Thr Ser Asp Cys Cys Glu Ala Leu Ser Leu Ala Leu
                165                 170                 175

Ser Cys Asn Arg His Leu Thr Ser Leu Asn Leu Val Gln Asn Asn Phe
            180                 185                 190

Ser Pro Lys Gly Met Met Lys Leu Cys Ser Ala Phe Ala Cys Pro Thr
        195                 200                 205

Ser Asn Leu Gln Ile Ile Gly Leu Trp Lys Trp Gln Tyr Pro Val Gln
    210                 215                 220

Ile Arg Lys Leu Leu Glu Glu Val Gln Leu Leu Lys Pro Arg Val Val
```

```
                  225                 230                 235                 240
         Ile Asp Gly Ser Trp His Ser Phe Asp Glu Asp Asp Arg Tyr Trp Trp
                         245                 250                 255

Lys Asn

<210> SEQ ID NO 5
<211> LENGTH: 3447
<212> TYPE: DNA
<213> ORGANISM: Mus musculus

<400> SEQUENCE: 5
aaagcacaat gggtcctcca gaaaagaaa  gtaaagcaat cttgaaagca cgtggattgg     60
aagaggaaca gaagtcagaa agaaaaatga cttctccaga aaacgacagt aaatcaatcc    120
agaaagacca aggaccagag caggagcaga catcagaaag cacaatgggt cctccagaaa    180
aagacagtaa agcaatcttg aaagcacgtg gattggaaga ggaacagaag tcagaaagca    240
caatgtctcc ttcagaaaat gtcagtagag caatcctgaa agacagtgga tcagaagaag    300
tggaacaggc gtcagaaaga aaatgactt  ctccagaaaa cgacagtaaa tcaatccaga    360
aagaccaagg accagagcag gagcagacat cagaaaccctt acaatctaag gaagaagatg    420
aagtgacaga ggcagataaa gataatggag gtgacttaca agactacaag cccatgtga     480 ttgctaagtt cgacacaagt gtggatctac actatgacag cccagagatg aaattattgt    540
ctgatgcttt taaccatac  cagaaaaacct tccagcctca caccattatc ctacatggaa    600
gaccaggagt tgggaagtca gctttggcca gaagtattgt tcttggctgg gcacagggta    660
aactcttcca aaaaatgtcc tttgtcatct tcttctctgt tagagaaata aagtggacag    720
agaagagcag tttggcacag ctgattgcta aggagtgtcc agactcctgg gatctagtga    780
caaagatcat gtcccaacca gaaagactct tgtttgtcat agatggcttg gatgatatgg    840
actctgtcct ccaacatgat gatatgacac tatccagaga ctggaaggat gaacagccca    900
tatacatcct gatgtacagc ctcctgagga aggctctctt acctcagtcc tttctcatca    960
ttaccaccag aaacacaggc ttagaaaaac tcaagtcaat ggttgtgtcc ccctctata    1020 tactggttga aggactgtct gcatcaagga gatctcagct ggtcctcgag aacatctcca    1080
atgagtctga tagaatacaa gtcttccatt ctctgataga aaatcaccag ctgtttgacc    1140
aatgccaggc ccctctgtgt gctccctgg  tctgtgaggc tctacagcta cagaagaaac    1200
tgggaaagag atgcacccta ccctgccaga ctctcaccgg tttgtatgcc acgttggtgt    1260 tcaccagct  cacccttgaaa aggccttccc agagcgctct cagtcaggaa gaacagatta    1320
ctctagtggg tttgtgcatg atggcagctg aaggagtgtg gaccatgagg tcggtgttct    1380
atgatgatga cctgaagaac tatagcctaa aggagtctga gatcttggcc ctctttcaca    1440
tgaacatcct tctccaggtt ggccacaaca gtgagcagtg ttatgttttc tcccacctca    1500
gcctgcagga tttctttgct gccttatatt atgttttaga agggctggag gaatggaatc    1560
agcatttttg cttcattgaa aaccaaagga gcatcatgga ggtgaagaga actgacgaca    1620
ctcgcctcct cgggatgaag cgtttcttat ttggcctcat gaacaaggat atcttgaaga    1680
ctctggaggt tctgtttgaa tatcccgtga ttccaactgt tgagcagaag ctccaacact    1740
gggtctctct gatagctcag caggtcaatg caccagccc  aatggacacc ctggatgcct    1800
tctattgtct atttgagtct caggatgaag agtttgttgg cggggctctc aaacgcttcc    1860
aagaagtgtg gctgctgatt aaccagaaga tggacttgaa ggtctcttcc tactgtctca    1920
```

-continued

```
agcactgtca gaacttgaag gcaatccggg tggatatcag agacctcctc tcggtagata    1980
atactctcga gctgtgccct gttgttactg tccaggagac acaatgtaag cccctcctca    2040
tggagtggtg gggaaacttc tgctctgtgc ttggcagcct ccggaacttg aaggagctgg    2100
acttgggcga cagcatcctg agtcaacggg ccatgaagat actgtgcctc gagctgcgga    2160
atcagtcctg cagaatacag aagctgacgt ttaagagtgc agaggtagtg tctggcctga    2220
aacatctctg gaagctcctt tttagcaatc aaaacttaaa gtacctcaat ctagggaaca    2280
ctcccatgaa ggatgatgac atgaagttag cctgcgaagc gctgaaacat ccaaagtgct    2340
ccgtggagac tctgaggttg gattcctgtg agttaaccat cattggttat gagatgatct    2400
ccacgcttct tatttcaacc accaggctaa agtgtctcag cctggccaaa aatagagtgg    2460
gagtaaaaag catgatatcc cttgggaatg ccttgagtag ctcaatgtgt ctactgcaaa    2520
agttgatact ggacaactgt ggcctcacac ctgccagctg ccaccttctg gtctcagccc    2580
ttttcagcaa ccagaacttg acacacctgt gcctgtcaaa caacagcctg gggactgaag    2640
gagtgcaaca gctgtgtcag ttcctgagga atccagaatg tgctctccag cggctgatac    2700
tgaatcactg caacattgta gatgatgctt atggcttcct ggcaatgaga cttgcaaaca    2760
acacaaagct gacccacctg agcctgacca tgaaccccgt aggggatggt gcaatgaagc    2820
tactgtgtga agctttaaag gaacctactt gttaccttca agaactgaa ctagtggact    2880
gccaactcac acagaactgc tgcgaggacc tggcctgtat gatcacaaca accaagcact    2940
taaaaagttt ggatcttggt aacaacgccc tgggtgacaa aggagtcata accctgtgtg    3000
agggactgaa gcaaagtagc agctccctga ggagacttgg gttgggggca tgtaagttga    3060
cttccaattg ctgtgaggca ttgtcattgg ccatctcttg caaccctcac ctgaacagcc    3120
taaacctggt gaagaatgac ttcagtacat cggggatgtt gaagctgtgc tctgcgttcc    3180
aatgccctgt ctctaacctg gggataattg gcctgtggaa gcaggagtac tatgcccgag    3240
tgagaagaca gctggaggaa gttgagtttg tcaagcccca cgtggtgatt gatggtgatt    3300
ggtatgctag tgatgaagat gaccgaaact ggtggaaaaa ctgaagacat gagcccctc    3360
tccttcacgt cctagcactg cagtatctgt gaaatgtttg tctcaccttg gaggatgtag    3420
caagaatgaa ataaacacag catttag                                        3447
```

<210> SEQ ID NO 6
<211> LENGTH: 1111
<212> TYPE: PRT
<213> ORGANISM: Mus musculus

<400> SEQUENCE: 6

```
Met Gly Pro Pro Glu Lys Glu Ser Lys Ala Ile Leu Lys Ala Arg Gly
1               5                   10                  15

Leu Glu Glu Glu Gln Lys Ser Glu Arg Lys Met Thr Ser Pro Glu Asn
            20                  25                  30

Asp Ser Lys Ser Ile Gln Lys Asp Gln Gly Pro Glu Gln Glu Gln Thr
        35                  40                  45

Ser Glu Ser Thr Met Gly Pro Pro Glu Lys Asp Ser Lys Ala Ile Leu
    50                  55                  60

Lys Ala Arg Gly Leu Glu Glu Glu Gln Lys Ser Glu Ser Thr Met Ser
65                  70                  75                  80

Pro Ser Glu Asn Val Ser Arg Ala Ile Leu Lys Asp Ser Gly Ser Glu
                85                  90                  95

Glu Val Glu Gln Ala Ser Glu Arg Lys Met Thr Ser Pro Glu Asn Asp
```

```
                100                 105                 110
Ser Lys Ser Ile Gln Lys Asp Gln Gly Pro Glu Gln Glu Gln Thr Ser
            115                 120                 125
Glu Thr Leu Gln Ser Lys Glu Glu Asp Glu Val Thr Glu Ala Asp Lys
            130                 135                 140
Asp Asn Gly Gly Asp Leu Gln Asp Tyr Lys Ala His Val Ile Ala Lys
145                 150                 155                 160
Phe Asp Thr Ser Val Asp Leu His Tyr Asp Ser Pro Glu Met Lys Leu
                165                 170                 175
Leu Ser Asp Ala Phe Lys Pro Tyr Gln Lys Thr Phe Gln Pro His Thr
            180                 185                 190
Ile Ile Leu His Gly Arg Pro Gly Val Gly Lys Ser Ala Leu Ala Arg
            195                 200                 205
Ser Ile Val Leu Gly Trp Ala Gln Gly Lys Leu Phe Gln Lys Met Ser
            210                 215                 220
Phe Val Ile Phe Phe Ser Val Arg Glu Ile Lys Trp Thr Glu Lys Ser
225                 230                 235                 240
Ser Leu Ala Gln Leu Ile Ala Lys Glu Cys Pro Asp Ser Trp Asp Leu
                245                 250                 255
Val Thr Lys Ile Met Ser Gln Pro Glu Arg Leu Leu Phe Val Ile Asp
                260                 265                 270
Gly Leu Asp Asp Met Asp Ser Val Leu Gln His Asp Asp Met Thr Leu
            275                 280                 285
Ser Arg Asp Trp Lys Asp Glu Gln Pro Ile Tyr Ile Leu Met Tyr Ser
            290                 295                 300
Leu Leu Arg Lys Ala Leu Leu Pro Gln Ser Phe Leu Ile Ile Thr Thr
305                 310                 315                 320
Arg Asn Thr Gly Leu Glu Lys Leu Lys Ser Met Val Val Ser Pro Leu
                325                 330                 335
Tyr Ile Leu Val Glu Gly Leu Ser Ala Ser Arg Arg Ser Gln Leu Val
                340                 345                 350
Leu Glu Asn Ile Ser Asn Glu Ser Asp Arg Ile Gln Val Phe His Ser
            355                 360                 365
Leu Ile Glu Asn His Gln Leu Phe Asp Gln Cys Gln Ala Pro Ser Val
            370                 375                 380
Cys Ser Leu Val Cys Glu Ala Leu Gln Leu Gln Lys Lys Leu Gly Lys
385                 390                 395                 400
Arg Cys Thr Leu Pro Cys Gln Thr Leu Thr Gly Leu Tyr Ala Thr Leu
                405                 410                 415
Val Phe His Gln Leu Thr Leu Lys Arg Pro Ser Gln Ser Ala Leu Ser
            420                 425                 430
Gln Glu Glu Gln Ile Thr Leu Val Gly Leu Cys Met Met Ala Ala Glu
            435                 440                 445
Gly Val Trp Thr Met Arg Ser Val Phe Tyr Asp Asp Asp Leu Lys Asn
            450                 455                 460
Tyr Ser Leu Lys Glu Ser Glu Ile Leu Ala Leu Phe His Met Asn Ile
465                 470                 475                 480
Leu Leu Gln Val Gly His Asn Ser Glu Gln Cys Tyr Val Phe Ser His
                485                 490                 495
Leu Ser Leu Gln Asp Phe Phe Ala Ala Leu Tyr Tyr Val Leu Glu Gly
            500                 505                 510
Leu Glu Glu Trp Asn Gln His Phe Cys Phe Ile Glu Asn Gln Arg Ser
            515                 520                 525
```

```
Ile Met Glu Val Lys Arg Thr Asp Asp Thr Arg Leu Leu Gly Met Lys
    530                 535                 540

Arg Phe Leu Phe Gly Leu Met Asn Lys Asp Ile Leu Lys Thr Leu Glu
545                 550                 555                 560

Val Leu Phe Glu Tyr Pro Val Ile Pro Thr Val Gln Lys Leu Gln
                565                 570                 575

His Trp Val Ser Leu Ile Ala Gln Gln Val Asn Gly Thr Ser Pro Met
                580                 585                 590

Asp Thr Leu Asp Ala Phe Tyr Cys Leu Phe Glu Ser Gln Asp Glu Glu
            595                 600                 605

Phe Val Gly Gly Ala Leu Lys Arg Phe Gln Glu Val Trp Leu Leu Ile
            610                 615                 620

Asn Gln Lys Met Asp Leu Lys Val Ser Ser Tyr Cys Leu Lys His Cys
625                 630                 635                 640

Gln Asn Leu Lys Ala Ile Arg Val Asp Ile Arg Asp Leu Leu Ser Val
                645                 650                 655

Asp Asn Thr Leu Glu Leu Cys Pro Val Val Thr Val Gln Glu Thr Gln
                660                 665                 670

Cys Lys Pro Leu Leu Met Glu Trp Trp Gly Asn Phe Cys Ser Val Leu
            675                 680                 685

Gly Ser Leu Arg Asn Leu Lys Glu Leu Asp Leu Gly Asp Ser Ile Leu
    690                 695                 700

Ser Gln Arg Ala Met Lys Ile Leu Cys Leu Glu Leu Arg Asn Gln Ser
705                 710                 715                 720

Cys Arg Ile Gln Lys Leu Thr Phe Lys Ser Ala Glu Val Val Ser Gly
                725                 730                 735

Leu Lys His Leu Trp Lys Leu Leu Phe Ser Asn Gln Asn Leu Lys Tyr
            740                 745                 750

Leu Asn Leu Gly Asn Thr Pro Met Lys Asp Asp Met Lys Leu Ala
    755                 760                 765

Cys Glu Ala Leu Lys His Pro Lys Cys Ser Val Glu Thr Leu Arg Leu
770                 775                 780

Asp Ser Cys Glu Leu Thr Ile Ile Gly Tyr Glu Met Ile Ser Thr Leu
785                 790                 795                 800

Leu Ile Ser Thr Thr Arg Leu Lys Cys Leu Ser Leu Ala Lys Asn Arg
                805                 810                 815

Val Gly Val Lys Ser Met Ile Ser Leu Gly Asn Ala Leu Ser Ser Ser
                820                 825                 830

Met Cys Leu Leu Gln Lys Leu Ile Leu Asp Asn Cys Gly Leu Thr Pro
            835                 840                 845

Ala Ser Cys His Leu Leu Val Ser Ala Leu Phe Ser Asn Gln Asn Leu
    850                 855                 860

Thr His Leu Cys Leu Ser Asn Asn Ser Leu Gly Thr Glu Gly Val Gln
865                 870                 875                 880

Gln Leu Cys Gln Phe Leu Arg Asn Pro Glu Cys Ala Leu Gln Arg Leu
                885                 890                 895

Ile Leu Asn His Cys Asn Ile Val Asp Asp Ala Tyr Gly Phe Leu Ala
            900                 905                 910

Met Arg Leu Ala Asn Asn Thr Lys Leu Thr His Leu Ser Leu Thr Met
    915                 920                 925

Asn Pro Val Gly Asp Gly Ala Met Lys Leu Leu Cys Glu Ala Leu Lys
    930                 935                 940
```

```
Glu Pro Thr Cys Tyr Leu Gln Glu Leu Glu Leu Val Asp Cys Gln Leu
945                 950                 955                 960

Thr Gln Asn Cys Cys Glu Asp Leu Ala Cys Met Ile Thr Thr Thr Lys
            965                 970                 975

His Leu Lys Ser Leu Asp Leu Gly Asn Asn Ala Leu Gly Asp Lys Gly
        980                 985                 990

Val Ile Thr Leu Cys Glu Gly Leu  Lys Gln Ser Ser  Ser Leu Arg
        995                 1000                1005

Arg Leu Gly Leu Gly Ala Cys  Lys Leu Thr Ser Asn  Cys Cys Glu
    1010                1015                1020

Ala Leu Ser Leu Ala Ile Ser  Cys Asn Pro His Leu  Asn Ser Leu
    1025                1030                1035

Asn Leu Val Lys Asn Asp Phe  Ser Thr Ser Gly Met  Leu Lys Leu
    1040                1045                1050

Cys Ser Ala Phe Gln Cys Pro  Val Ser Asn Leu Gly  Ile Ile Gly
    1055                1060                1065

Leu Trp Lys Gln Glu Tyr Tyr  Ala Arg Val Arg  Gln Leu Glu
    1070                1075                1080

Glu Val Glu Phe Val Lys Pro  His Val Val Ile Asp  Gly Asp Trp
    1085                1090                1095

Tyr Ala Ser Asp Glu Asp Asp  Arg Asn Trp Trp Lys  Asn
    1100                1105                1110

<210> SEQ ID NO 7
<211> LENGTH: 22
<212> TYPE: DNA
<213> ORGANISM: synthetic oligonucleotide

<400> SEQUENCE: 7
tttcacatga acatccttct cc                                          22

<210> SEQ ID NO 8
<211> LENGTH: 21
<212> TYPE: DNA
<213> ORGANISM: synthetic oligonucleotide

<400> SEQUENCE: 8
agtgctggag gcagaaggaa g                                           21

<210> SEQ ID NO 9
<211> LENGTH: 26
<212> TYPE: DNA
<213> ORGANISM: synthetic oligonucleotide

<400> SEQUENCE: 9
caggaattgg gaaatcggct ctctag                                      26

<210> SEQ ID NO 10
<211> LENGTH: 27
<212> TYPE: DNA
<213> ORGANISM: synthetic oligonucleotide

<400> SEQUENCE: 10
ccaaatgctt tgtgtttatt taattcc                                     27

<210> SEQ ID NO 11
<211> LENGTH: 19
<212> TYPE: DNA
<213> ORGANISM: synthetic oligonucleotide
```

```
<400> SEQUENCE: 11
cggaattcgt cactcagcg                                              19

<210> SEQ ID NO 12
<211> LENGTH: 18
<212> TYPE: DNA
<213> ORGANISM: synthetic oligonucleotide

<400> SEQUENCE: 12
agcgcgtgaa tcagatcg                                               18

<210> SEQ ID NO 13
<211> LENGTH: 24
<212> TYPE: DNA
<213> ORGANISM: synthetic oligonucleotide

<400> SEQUENCE: 13
attccctggt agagtccacc ttgc                                        24

<210> SEQ ID NO 14
<211> LENGTH: 24
<212> TYPE: DNA
<213> ORGANISM: synthetic oligonucleotide

<400> SEQUENCE: 14
acagcacgat ccttctggct agag                                        24

<210> SEQ ID NO 15
<211> LENGTH: 23
<212> TYPE: DNA
<213> ORGANISM: synthetic oligonucleotide

<400> SEQUENCE: 15
caagctccgg tgacggagat cat                                         23

<210> SEQ ID NO 16
<211> LENGTH: 22
<212> TYPE: DNA
<213> ORGANISM: synthetic oligonucleotide

<400> SEQUENCE: 16
agctggaggc agaaggaaga tg                                          22

<210> SEQ ID NO 17
<211> LENGTH: 27
<212> TYPE: DNA
<213> ORGANISM: synthetic oligonucleotide

<400> SEQUENCE: 17
tctggcctca gccctcgtca gcttgac                                     27

<210> SEQ ID NO 18
<211> LENGTH: 27
<212> TYPE: DNA
<213> ORGANISM: synthetic oligonucleotide

<400> SEQUENCE: 18
ccaaatgctt tgtgtttatt taattcc                                     27

<210> SEQ ID NO 19
<211> LENGTH: 21
<212> TYPE: DNA
<213> ORGANISM: synthetic oligonucleotide
```

<400> SEQUENCE: 19
tctggcctca gccctcgtca g                                                    21

<210> SEQ ID NO 20
<211> LENGTH: 21
<212> TYPE: DNA
<213> ORGANISM: synthetic oligonucleotide

<400> SEQUENCE: 20
actgaagtta ttctgcacca g                                                    21

<210> SEQ ID NO 21
<211> LENGTH: 20
<212> TYPE: DNA
<213> ORGANISM: synthetic oligonucleotide

<400> SEQUENCE: 21
tgacttctga ttgctgtgag                                                      20

<210> SEQ ID NO 22
<211> LENGTH: 20
<212> TYPE: DNA
<213> ORGANISM: synthetic oligonucleotide

<400> SEQUENCE: 22
ttccaccagt accggtcatc                                                      20

<210> SEQ ID NO 23
<211> LENGTH: 3900
<212> TYPE: DNA
<213> ORGANISM: homo sapiens
<220> FEATURE:
<221> NAME/KEY: CDS
<222> LOCATION: (1)..(3600)

<400> SEQUENCE: 23

```
atg aag gtt gca gga gga ctt gaa ctt gga gct gct gct ctg ctc tca         48
Met Lys Val Ala Gly Gly Leu Glu Leu Gly Ala Ala Ala Leu Leu Ser
1               5                   10                  15 gca tca cca cgt gct ctt gtc act ctt tcc aca ggt cct act tgc tct         96
Ala Ser Pro Arg Ala Leu Val Thr Leu Ser Thr Gly Pro Thr Cys Ser
                20                  25                  30 ata tta cca aag aat cca ctt ttc ccc caa aac ctg agc tct cag cct         144
Ile Leu Pro Lys Asn Pro Leu Phe Pro Gln Asn Leu Ser Ser Gln Pro
            35                  40                  45 tgt atc aag atg gaa gga gac aaa tcg ctc acc ttt tcc agc tac ggg         192
Cys Ile Lys Met Glu Gly Asp Lys Ser Leu Thr Phe Ser Ser Tyr Gly
        50                  55                  60 ctg caa tgg tgt ctc tat gag cta gac aag gaa gaa ttt cag aca ttc         240
Leu Gln Trp Cys Leu Tyr Glu Leu Asp Lys Glu Glu Phe Gln Thr Phe
65                  70                  75                  80 aag gaa tta cta aag aag aaa tct tca gaa tcg acc aca tgc tct att         288
Lys Glu Leu Leu Lys Lys Lys Ser Ser Glu Ser Thr Thr Cys Ser Ile
                85                  90                  95 cca cag ttt gaa atc gag aat gcc aac gtg gaa tgt ctg gca ctc ctc         336
Pro Gln Phe Glu Ile Glu Asn Ala Asn Val Glu Cys Leu Ala Leu Leu
                100                 105                 110 ttg cat gag tat tat gga gca tcg ctg gcc tgg gct acg tcc att agc         384
Leu His Glu Tyr Tyr Gly Ala Ser Leu Ala Trp Ala Thr Ser Ile Ser
            115                 120                 125 atc ttt gaa aac atg aac ctg cga acc ctc tcg gag aag gca cgg gat         432
```

|     |     |
| --- | --- |
| Ile Phe Glu Asn Met Asn Leu Arg Thr Leu Ser Glu Lys Ala Arg Asp<br>    130                 135                 140 | |
| gac atg aaa aga cat tca cca gaa gat cct gaa gca acg atg act gac<br>Asp Met Lys Arg His Ser Pro Glu Asp Pro Glu Ala Thr Met Thr Asp<br>145                 150                 155                 160 | 480 |
| caa gga cca agc aag gaa aaa gtg cca gga att tca caa gct gtg caa<br>Gln Gly Pro Ser Lys Glu Lys Val Pro Gly Ile Ser Gln Ala Val Gln<br>                165                 170                 175 | 528 |
| caa gat agt gcc aca gct gca gag aca aaa gaa cag gaa att tca caa<br>Gln Asp Ser Ala Thr Ala Ala Glu Thr Lys Glu Gln Glu Ile Ser Gln<br>            180                 185                 190 | 576 |
| gct atg gaa caa gaa ggt gcc aca gca gca gag aca gaa gaa caa gaa<br>Ala Met Glu Gln Glu Gly Ala Thr Ala Ala Glu Thr Glu Glu Gln Glu<br>        195                 200                 205 | 624 |
| att tca caa gct atg gaa caa gaa ggt gcc aca gca gca gag aca gaa<br>Ile Ser Gln Ala Met Glu Gln Glu Gly Ala Thr Ala Ala Glu Thr Glu<br>    210                 215                 220 | 672 |
| gaa caa gga cat gga ggt gac aca tgg gac tac aag agt cac gtg atg<br>Glu Gln Gly His Gly Gly Asp Thr Trp Asp Tyr Lys Ser His Val Met<br>225                 230                 235                 240 | 720 |
| acc aaa ttc gct gag gag gag gat gta cgt cgt agt ttt gaa aac act<br>Thr Lys Phe Ala Glu Glu Glu Asp Val Arg Arg Ser Phe Glu Asn Thr<br>                245                 250                 255 | 768 |
| gct gct gac tgg ccg gaa atg caa acg ttg gct ggt gct ttt gat tca<br>Ala Ala Asp Trp Pro Glu Met Gln Thr Leu Ala Gly Ala Phe Asp Ser<br>            260                 265                 270 | 816 |
| gac cgg tgg ggc ttc cgg cct cgc acg gtg gtt ctg cac gga aag tca<br>Asp Arg Trp Gly Phe Arg Pro Arg Thr Val Val Leu His Gly Lys Ser<br>        275                 280                 285 | 864 |
| gga att ggg aaa tcg gct cta gcc aga agg atc gtg ctg tgc tgg gcg<br>Gly Ile Gly Lys Ser Ala Leu Ala Arg Arg Ile Val Leu Cys Trp Ala<br>    290                 295                 300 | 912 |
| caa ggt gga ctc tac cag gga atg ttc tcc tac gtc ttc ttc ctc ccc<br>Gln Gly Gly Leu Tyr Gln Gly Met Phe Ser Tyr Val Phe Phe Leu Pro<br>305                 310                 315                 320 | 960 |
| gtt aga gag atg cag cgg aag aag gag agc agt gtc aca gag ttc atc<br>Val Arg Glu Met Gln Arg Lys Lys Glu Ser Ser Val Thr Glu Phe Ile<br>                325                 330                 335 | 1008 |
| tcc agg gag tgg cca gac tcc cag gct ccg gtg acg gag atc atg tcc<br>Ser Arg Glu Trp Pro Asp Ser Gln Ala Pro Val Thr Glu Ile Met Ser<br>            340                 345                 350 | 1056 |
| cga cca gaa agg ctg ttg ttc atc att gac ggt ttc gat gac ctg ggc<br>Arg Pro Glu Arg Leu Leu Phe Ile Ile Asp Gly Phe Asp Asp Leu Gly<br>        355                 360                 365 | 1104 |
| tct gtc ctc aac aat gac aca aag ctc tgc aaa gac tgg gct gag aag<br>Ser Val Leu Asn Asn Asp Thr Lys Leu Cys Lys Asp Trp Ala Glu Lys<br>    370                 375                 380 | 1152 |
| cag cct ccg ttc acc ctc ata cgc agt ctg ctg agg aag gtc ctg ctc<br>Gln Pro Pro Phe Thr Leu Ile Arg Ser Leu Leu Arg Lys Val Leu Leu<br>385                 390                 395                 400 | 1200 |
| cct gag tcc ttc ctg atc gtc acc gtc aga gac gtg ggc aca gag aag<br>Pro Glu Ser Phe Leu Ile Val Thr Val Arg Asp Val Gly Thr Glu Lys<br>                405                 410                 415 | 1248 |
| ctc aag tca gag gtc gtg tct ccc cgt tac ctg tta gtt aga gga atc<br>Leu Lys Ser Glu Val Val Ser Pro Arg Tyr Leu Leu Val Arg Gly Ile<br>            420                 425                 430 | 1296 |
| tcc ggg gaa caa aga atc cac ttg ctc ctt gag cgc ggg att ggt gag<br>Ser Gly Glu Gln Arg Ile His Leu Leu Leu Glu Arg Gly Ile Gly Glu<br>        435                 440                 445 | 1344 |

```
cat cag aag aca caa ggg ttg cgt gcg atc atc aac aac cgt gag ctg    1392
His Gln Lys Thr Gln Gly Leu Arg Ala Ile Ile Asn Asn Arg Glu Leu
    450                 455                 460 ctc gac cag tgc cag gtg ccc gcc gtg ggc tct ctc atc tgc gtg gcc    1440
Leu Asp Gln Cys Gln Val Pro Ala Val Gly Ser Leu Ile Cys Val Ala
465                 470                 475                 480 ctg cag ctg cag gac gtg gtg ggg gag agc gtc gcc ccc ttc aac caa    1488
Leu Gln Leu Gln Asp Val Val Gly Glu Ser Val Ala Pro Phe Asn Gln
                485                 490                 495 acg ctc aca ggc ctg cac gcc gct ttt gcg ttt cat cag ctc acc cct    1536
Thr Leu Thr Gly Leu His Ala Ala Phe Ala Phe His Gln Leu Thr Pro
            500                 505                 510 cga ggc gtg gtc cgg cgc tgt ctc aat ctg gag gaa aga gtt gtc ctg    1584
Arg Gly Val Val Arg Arg Cys Leu Asn Leu Glu Glu Arg Val Val Leu
        515                 520                 525 aag cgc ttc tgc cgt atg gct gtg gag gga gtg tgg aat agg aag tca    1632
Lys Arg Phe Cys Arg Met Ala Val Glu Gly Val Trp Asn Arg Lys Ser
    530                 535                 540 gtg ttt gat ggt gac gac ctc atg gtt caa gga ctc ggg gag tct gag    1680
Val Phe Asp Gly Asp Asp Leu Met Val Gln Gly Leu Gly Glu Ser Glu
545                 550                 555                 560 ctc cgt gct ctg ttt cac atg aac atc ctt ctc cca gac agc cac tgt    1728
Leu Arg Ala Leu Phe His Met Asn Ile Leu Leu Pro Asp Ser His Cys
                565                 570                 575 gag gag tac tac acc ttc ttc cac ctc agt ctc cag gac ttc tgt gcc    1776
Glu Glu Tyr Tyr Thr Phe Phe His Leu Ser Leu Gln Asp Phe Cys Ala
            580                 585                 590 gcc ttg tac tac gtg tta gag ggc ctg gaa atc gag cca gct ctc tgc    1824
Ala Leu Tyr Tyr Val Leu Glu Gly Leu Glu Ile Glu Pro Ala Leu Cys
        595                 600                 605 cct ctg tac gtt gag aag aca aag agg tcc atg gag ctt aaa cag gca    1872
Pro Leu Tyr Val Glu Lys Thr Lys Arg Ser Met Glu Leu Lys Gln Ala
    610                 615                 620 ggc ttc cat atc cac tcg ctt tgg atg aag cgt ttc ttg ttt ggc ctc    1920
Gly Phe His Ile His Ser Leu Trp Met Lys Arg Phe Leu Phe Gly Leu
625                 630                 635                 640 gtg agc gaa gac gta agg agg cca ctg gag gtc ctg ctg ggc tgt ccc    1968
Val Ser Glu Asp Val Arg Arg Pro Leu Glu Val Leu Leu Gly Cys Pro
                645                 650                 655 gtt ccc ctg ggg gtg aag cag aag ctt ctg cac tgg gtc tct ctg ttg    2016
Val Pro Leu Gly Val Lys Gln Lys Leu Leu His Trp Val Ser Leu Leu
            660                 665                 670 ggt cag cag cct aat gcc acc acc cca gga gac acc ctg gac gcc ttc    2064
Gly Gln Gln Pro Asn Ala Thr Thr Pro Gly Asp Thr Leu Asp Ala Phe
        675                 680                 685 cac tgt ctt ttc gag act caa gac aaa gag ttt gtt cgc ttg gca tta    2112
His Cys Leu Phe Glu Thr Gln Asp Lys Glu Phe Val Arg Leu Ala Leu
    690                 695                 700 aac agc ttc caa gaa gtg tgg ctt ccg att aac cag aac ctg gac ttg    2160
Asn Ser Phe Gln Glu Val Trp Leu Pro Ile Asn Gln Asn Leu Asp Leu
705                 710                 715                 720 ata gca tct tcc ttc tgc ctc cag cac tgt ccg tat ttg cgg aaa att    2208
Ile Ala Ser Ser Phe Cys Leu Gln His Cys Pro Tyr Leu Arg Lys Ile
                725                 730                 735 cgg gtg gat gtc aaa ggg atc ttc cca aga gat gag tcc gct gag gca    2256
Arg Val Asp Val Lys Gly Ile Phe Pro Arg Asp Glu Ser Ala Glu Ala
            740                 745                 750 tgt cct gtg gtc cct cta tgg atg cgg gat aag acc ctc att gag gag    2304
Cys Pro Val Val Pro Leu Trp Met Arg Asp Lys Thr Leu Ile Glu Glu
        755                 760                 765
```

```
cag tgg gaa gat ttc tgc tcc atg ctt ggc acc cac cca cac ctg cgg    2352
Gln Trp Glu Asp Phe Cys Ser Met Leu Gly Thr His Pro His Leu Arg
    770                 775                 780 cag ctg gac ctg ggc agc agc atc ctg aca gag cgg gcc atg aag acc    2400
Gln Leu Asp Leu Gly Ser Ser Ile Leu Thr Glu Arg Ala Met Lys Thr
785                 790                 795                 800 ctg tgt gcc aag ctg agg cat ccc acc tgc aag ata cag acc ctg atg    2448
Leu Cys Ala Lys Leu Arg His Pro Thr Cys Lys Ile Gln Thr Leu Met
                    805                 810                 815 ttt aga aat gca cag att acc cct ggt gtg caa cac ctc tgg aga atc    2496
Phe Arg Asn Ala Gln Ile Thr Pro Gly Val Gln His Leu Trp Arg Ile
                820                 825                 830 gtc atg gcc aac cgt aac cta aga tcc ctc aac ttg gga ggc acc cac    2544
Val Met Ala Asn Arg Asn Leu Arg Ser Leu Asn Leu Gly Gly Thr His
            835                 840                 845 ctg aag gaa gag gat gta agg atg gcg tgt gaa gcc tta aaa cac cca    2592
Leu Lys Glu Glu Asp Val Arg Met Ala Cys Glu Ala Leu Lys His Pro
850                 855                 860 aaa tgt ttg ttg gag tct ttg agg ctg gat tgc gtg gga ttg acc cat    2640
Lys Cys Leu Leu Glu Ser Leu Arg Leu Asp Cys Cys Gly Leu Thr His
865                 870                 875                 880 gcc tgt tac ctg aag atc tcc caa atc ctt acg acc tcc ccc agc ctg    2688
Ala Cys Tyr Leu Lys Ile Ser Gln Ile Leu Thr Thr Ser Pro Ser Leu
                    885                 890                 895 aaa tct ctg agc ctg gca gga aac aag gtg aca gac cag gga gta acg    2736
Lys Ser Leu Ser Leu Ala Gly Asn Lys Val Thr Asp Gln Gly Val Thr
                900                 905                 910 cct ctc agt gat gcc ttg agg gtc tcc cag tgc gcc ctg cag aag ctg    2784
Pro Leu Ser Asp Ala Leu Arg Val Ser Gln Cys Ala Leu Gln Lys Leu
            915                 920                 925 ata ctg gag gac tgt ggc atc aca gcc acg ggt tgc cag agt ctg gcc    2832
Ile Leu Glu Asp Cys Gly Ile Thr Ala Thr Gly Cys Gln Ser Leu Ala
930                 935                 940 tca gcc ctc gtc agc aac cgg agc ttg aca cac ctg tgc cta tcc aac    2880
Ser Ala Leu Val Ser Asn Arg Ser Leu Thr His Leu Cys Leu Ser Asn
945                 950                 955                 960 aac agc ctg ggg aac gaa ggt gta aat cta ctg tgt cga tcc atg agg    2928
Asn Ser Leu Gly Asn Glu Gly Val Asn Leu Leu Cys Arg Ser Met Arg
                    965                 970                 975 ctt ccc cac tgt agt ctg cag agg ctg atg ctg aat cag tgc cac ctg    2976
Leu Pro His Cys Ser Leu Gln Arg Leu Met Leu Asn Gln Cys His Leu
                980                 985                 990 gac acg gct ggc tgt ggt tct ctt gca ctt gcg ctt atg ggt aac tca    3024
Asp Thr Ala Gly Cys Gly Ser Leu Ala Leu Ala Leu Met Gly Asn Ser
            995                 1000                1005 tgg ctg acg cac ctg agc ctt agc atg aac cct gtg gaa gac aat        3069
Trp Leu Thr His Leu Ser Leu Ser Met Asn Pro Val Glu Asp Asn
    1010                1015                1020 ggc gtg aag ctt ctg tgc gag gtc atg aga gaa cca tct tgt cat        3114
Gly Val Lys Leu Leu Cys Glu Val Met Arg Glu Pro Ser Cys His
    1025                1030                1035 ctc cag gac ctg gag ttg gta aag tgt cat ctc acc gcc gcg tgc        3159
Leu Gln Asp Leu Glu Leu Val Lys Cys His Leu Thr Ala Ala Cys
    1040                1045                1050 tgt gag agt ctg tcc tgt gtg atc tcg agg agc aga cac ctg aag        3204
Cys Glu Ser Leu Ser Cys Val Ile Ser Arg Ser Arg His Leu Lys
    1055                1060                1065 agc ctg gat ctc acg gac aat gcc ctg ggt gac ggt ggg gtt gct        3249
Ser Leu Asp Leu Thr Asp Asn Ala Leu Gly Asp Gly Gly Val Ala
```

-continued

```
        1070                1075                1080
gcg ctg tgc gag gga ctg aag caa aag aac agt gtt ctg acg aga       3294
Ala Leu Cys Glu Gly Leu Lys Gln Lys Asn Ser Val Leu Thr Arg
    1085                1090                1095 ctc ggg ttg aag gca tgt gga ctg act tct gat tgc tgt gag gca       3339
Leu Gly Leu Lys Ala Cys Gly Leu Thr Ser Asp Cys Cys Glu Ala
    1100                1105                1110 ctc tcc ttg gcc ctt tcc tgc aac cgg cat ctg acc agt cta aac       3384
Leu Ser Leu Ala Leu Ser Cys Asn Arg His Leu Thr Ser Leu Asn
    1115                1120                1125 ctg gtg cag aat aac ttc agt ccc aaa gga atg atg aag ctg tgt       3429
Leu Val Gln Asn Asn Phe Ser Pro Lys Gly Met Met Lys Leu Cys
    1130                1135                1140 tcg gcc ttt gcc tgt ccc acg tct aac tta cag ata att ggg ctg       3474
Ser Ala Phe Ala Cys Pro Thr Ser Asn Leu Gln Ile Ile Gly Leu
    1145                1150                1155 tgg aaa tgg cag tac cct gtg caa ata agg aag ctg ctg gag gaa       3519
Trp Lys Trp Gln Tyr Pro Val Gln Ile Arg Lys Leu Leu Glu Glu
    1160                1165                1170 gtg cag cta ctc aag ccc cga gtc gta att gac ggt agt tgg cat       3564
Val Gln Leu Leu Lys Pro Arg Val Val Ile Asp Gly Ser Trp His
    1175                1180                1185 tct ttt gat gaa gat gac cgg tac tgg tgg aaa aac tgaagatacg        3610
Ser Phe Asp Glu Asp Asp Arg Tyr Trp Trp Lys Asn
    1190                1195                1200 gaaacctgcc ccactcacac ccatctgatg gaggaacttt aaacgctgtt ttctcagagc   3670
aagctatgca cctgggagtt ccttctcaaa gatggagaat gatttctgat tctcacaaag   3730
ccctcaatgg tagtgattct tctgtgttca ctctacgttg gttactggat tgaaggcta    3790
gagaccttca agtcatagga ctcagtatct gtgaaatgtc cgtcatatct cagagcatat   3850
agagggaatt aaataaacac aaagcatttg gaaaaaaaaa aaaaaaaaa              3900
```

<210> SEQ ID NO 24
<211> LENGTH: 1200
<212> TYPE: PRT
<213> ORGANISM: homo sapiens

<400> SEQUENCE: 24

```
Met Lys Val Ala Gly Gly Leu Glu Leu Gly Ala Ala Ala Leu Leu Ser
1               5                   10                  15

Ala Ser Pro Arg Ala Leu Val Thr Leu Ser Thr Gly Pro Thr Cys Ser
            20                  25                  30

Ile Leu Pro Lys Asn Pro Leu Phe Pro Gln Asn Leu Ser Ser Gln Pro
        35                  40                  45

Cys Ile Lys Met Glu Gly Asp Lys Ser Leu Thr Phe Ser Ser Tyr Gly
    50                  55                  60

Leu Gln Trp Cys Leu Tyr Glu Leu Asp Lys Glu Glu Phe Gln Thr Phe
65                  70                  75                  80

Lys Glu Leu Leu Lys Lys Lys Ser Ser Glu Ser Thr Thr Cys Ser Ile
                85                  90                  95

Pro Gln Phe Glu Ile Glu Asn Ala Asn Val Glu Cys Leu Ala Leu Leu
            100                 105                 110

Leu His Glu Tyr Tyr Gly Ala Ser Leu Ala Trp Ala Thr Ser Ile Ser
        115                 120                 125

Ile Phe Glu Asn Met Asn Leu Arg Thr Leu Ser Glu Lys Ala Arg Asp
    130                 135                 140
```

-continued

```
Asp Met Lys Arg His Ser Pro Glu Asp Pro Glu Ala Thr Met Thr Asp
145                 150                 155                 160

Gln Gly Pro Ser Lys Glu Lys Val Pro Gly Ile Ser Gln Ala Val Gln
            165                 170                 175

Gln Asp Ser Ala Thr Ala Ala Glu Thr Lys Glu Gln Glu Ile Ser Gln
        180                 185                 190

Ala Met Glu Gln Glu Gly Ala Thr Ala Ala Glu Thr Glu Glu Gln Glu
    195                 200                 205

Ile Ser Gln Ala Met Glu Gln Glu Gly Ala Thr Ala Ala Glu Thr Glu
210                 215                 220

Glu Gln Gly His Gly Gly Asp Thr Trp Asp Tyr Lys Ser His Val Met
225                 230                 235                 240

Thr Lys Phe Ala Glu Glu Asp Val Arg Arg Ser Phe Glu Asn Thr
            245                 250                 255

Ala Ala Asp Trp Pro Glu Met Gln Thr Leu Ala Gly Ala Phe Asp Ser
            260                 265                 270

Asp Arg Trp Gly Phe Arg Pro Arg Thr Val Val Leu His Gly Lys Ser
        275                 280                 285

Gly Ile Gly Lys Ser Ala Leu Ala Arg Arg Ile Val Leu Cys Trp Ala
    290                 295                 300

Gln Gly Gly Leu Tyr Gln Gly Met Phe Ser Tyr Val Phe Phe Leu Pro
305                 310                 315                 320

Val Arg Glu Met Gln Arg Lys Lys Glu Ser Ser Val Thr Glu Phe Ile
            325                 330                 335

Ser Arg Glu Trp Pro Asp Ser Gln Ala Pro Val Thr Glu Ile Met Ser
            340                 345                 350

Arg Pro Glu Arg Leu Leu Phe Ile Ile Asp Gly Phe Asp Asp Leu Gly
        355                 360                 365

Ser Val Leu Asn Asn Asp Thr Lys Leu Cys Lys Asp Trp Ala Glu Lys
    370                 375                 380

Gln Pro Pro Phe Thr Leu Ile Arg Ser Leu Leu Arg Lys Val Leu Leu
385                 390                 395                 400

Pro Glu Ser Phe Leu Ile Val Thr Val Arg Asp Val Gly Thr Glu Lys
            405                 410                 415

Leu Lys Ser Glu Val Val Ser Pro Arg Tyr Leu Leu Val Arg Gly Ile
            420                 425                 430

Ser Gly Glu Gln Arg Ile His Leu Leu Leu Glu Arg Gly Ile Gly Glu
        435                 440                 445

His Gln Lys Thr Gln Gly Leu Arg Ala Ile Ile Asn Asn Arg Glu Leu
    450                 455                 460

Leu Asp Gln Cys Gln Val Pro Ala Val Gly Ser Leu Ile Cys Val Ala
465                 470                 475                 480

Leu Gln Leu Gln Asp Val Val Gly Glu Ser Val Ala Pro Phe Asn Gln
            485                 490                 495

Thr Leu Thr Gly Leu His Ala Ala Phe Ala Phe His Gln Leu Thr Pro
            500                 505                 510

Arg Gly Val Val Arg Arg Cys Leu Asn Leu Glu Glu Arg Val Val Leu
        515                 520                 525

Lys Arg Phe Cys Arg Met Ala Val Glu Gly Val Trp Asn Arg Lys Ser
    530                 535                 540

Val Phe Asp Gly Asp Asp Leu Met Val Gln Gly Leu Gly Glu Ser Glu
545                 550                 555                 560

Leu Arg Ala Leu Phe His Met Asn Ile Leu Leu Pro Asp Ser His Cys
```

```
                565                 570                 575
Glu Glu Tyr Tyr Thr Phe Phe His Leu Ser Leu Gln Asp Phe Cys Ala
            580                 585                 590
Ala Leu Tyr Tyr Val Leu Glu Gly Leu Glu Ile Glu Pro Ala Leu Cys
            595                 600                 605
Pro Leu Tyr Val Glu Lys Thr Lys Arg Ser Met Glu Leu Lys Gln Ala
            610                 615                 620
Gly Phe His Ile His Ser Leu Trp Met Lys Arg Phe Leu Phe Gly Leu
625                 630                 635                 640
Val Ser Glu Asp Val Arg Arg Pro Leu Glu Val Leu Leu Gly Cys Pro
                645                 650                 655
Val Pro Leu Gly Val Lys Gln Lys Leu Leu His Trp Val Ser Leu Leu
            660                 665                 670
Gly Gln Gln Pro Asn Ala Thr Thr Pro Gly Asp Thr Leu Asp Ala Phe
            675                 680                 685
His Cys Leu Phe Glu Thr Gln Asp Lys Glu Phe Val Arg Leu Ala Leu
            690                 695                 700
Asn Ser Phe Gln Glu Val Trp Leu Pro Ile Asn Gln Asn Leu Asp Leu
705                 710                 715                 720
Ile Ala Ser Ser Phe Cys Leu Gln His Cys Pro Tyr Leu Arg Lys Ile
                725                 730                 735
Arg Val Asp Val Lys Gly Ile Phe Pro Arg Asp Glu Ser Ala Glu Ala
            740                 745                 750
Cys Pro Val Val Pro Leu Trp Met Arg Asp Lys Thr Leu Ile Glu Glu
            755                 760                 765
Gln Trp Glu Asp Phe Cys Ser Met Leu Gly Thr His Pro His Leu Arg
            770                 775                 780
Gln Leu Asp Leu Gly Ser Ser Ile Leu Thr Glu Arg Ala Met Lys Thr
785                 790                 795                 800
Leu Cys Ala Lys Leu Arg His Pro Thr Cys Lys Ile Gln Thr Leu Met
                805                 810                 815
Phe Arg Asn Ala Gln Ile Thr Pro Gly Val Gln His Leu Trp Arg Ile
            820                 825                 830
Val Met Ala Asn Arg Asn Leu Arg Ser Leu Asn Leu Gly Gly Thr His
            835                 840                 845
Leu Lys Glu Glu Asp Val Arg Met Ala Cys Glu Ala Leu Lys His Pro
850                 855                 860
Lys Cys Leu Leu Glu Ser Leu Arg Leu Asp Cys Cys Gly Leu Thr His
865                 870                 875                 880
Ala Cys Tyr Leu Lys Ile Ser Gln Ile Leu Thr Thr Ser Pro Ser Leu
                885                 890                 895
Lys Ser Leu Ser Leu Ala Gly Asn Lys Val Thr Asp Gln Gly Val Thr
            900                 905                 910
Pro Leu Ser Asp Ala Leu Arg Val Ser Gln Cys Ala Leu Gln Lys Leu
            915                 920                 925
Ile Leu Glu Asp Cys Gly Ile Thr Ala Thr Gly Cys Gln Ser Leu Ala
930                 935                 940
Ser Ala Leu Val Ser Asn Arg Ser Leu Thr His Leu Cys Leu Ser Asn
945                 950                 955                 960
Asn Ser Leu Gly Asn Glu Gly Val Asn Leu Leu Cys Arg Ser Met Arg
                965                 970                 975
Leu Pro His Cys Ser Leu Gln Arg Leu Met Leu Asn Gln Cys His Leu
            980                 985                 990
```

```
Asp Thr Ala Gly Cys Gly Ser Leu  Ala Leu Ala Leu Met  Gly Asn Ser
        995             1000              1005

Trp Leu Thr His Leu Ser Leu  Ser Met Asn Pro Val  Glu Asp Asn
    1010             1015             1020

Gly Val Lys Leu Leu Cys Glu  Val Met Arg Glu Pro  Ser Cys His
    1025             1030             1035

Leu Gln Asp Leu Glu Leu Val  Lys Cys His Leu Thr  Ala Ala Cys
    1040             1045             1050

Cys Glu Ser Leu Ser Cys Val  Ile Ser Arg Ser Arg  His Leu Lys
    1055             1060             1065

Ser Leu Asp Leu Thr Asp Asn  Ala Leu Gly Asp Gly  Gly Val Ala
    1070             1075             1080

Ala Leu Cys Glu Gly Leu Lys  Gln Lys Asn Ser Val  Leu Thr Arg
    1085             1090             1095

Leu Gly Leu Lys Ala Cys Gly  Leu Thr Ser Asp Cys  Cys Glu Ala
    1100             1105             1110

Leu Ser Leu Ala Leu Ser Cys  Asn Arg His Leu Thr  Ser Leu Asn
    1115             1120             1125

Leu Val Gln Asn Asn Phe Ser  Pro Lys Gly Met Met  Lys Leu Cys
    1130             1135             1140

Ser Ala Phe Ala Cys Pro Thr  Ser Asn Leu Gln Ile  Ile Gly Leu
    1145             1150             1155

Trp Lys Trp Gln Tyr Pro Val  Gln Ile Arg Lys Leu  Leu Glu Glu
    1160             1165             1170

Val Gln Leu Leu Lys Pro Arg  Val Val Ile Asp Gly  Ser Trp His
    1175             1180             1185

Ser Phe Asp Glu Asp Asp Arg  Tyr Trp Trp Lys Asn
    1190             1195             1200
```

The invention claimed is:

1. A method for detecting an autoimmune response to MATER in a subject, comprising determining whether the subject has circulating autoantibodies that recognize an epitope of a MATER protein, comprising contacting a sample from the subject with the isolated MATER protein of SEQ ID NO: 24 and detecting binding of the MATER protein to autoantibodies that recognize an epitope of a MATER protein in the sample, thereby detecting an autoimmune response to MATER in the subject.

2. The method of claim 1, wherein presence of autoantibodies that recognize an epitope of a MATER protein in the sample indicates infertility or reduced fertility of the subject, or an increased susceptibility of the subject to infertility or reduced fertility.

3. The method of claim 1, comprising determining whether the subject has circulating autoantibodies that recognize an epitope of the MATER protein by an ELISA.

4. The method of claim 1, wherein the subject is a mammal.

5. The method of claim 4, wherein the mammal is a human or a mouse.

* * * * *